United States Patent
Von Knethen et al.

(10) Patent No.: US 10,632,174 B2
(45) Date of Patent: Apr. 28, 2020

(54) B7-H1 FUSION POLYPEPTIDES FOR TREATING AND PREVENTING ORGAN FAILURE

(71) Applicant: Fraunhofer-Gesellschaft zur Förderung der angewandten Forschung e.V., München (DE)

(72) Inventors: Andreas Von Knethen, Nidderau (DE); Michael Parnham, Bad Soden/Ts. (DE); Lisa Katharina Sha, Hattgenstein (DE)

(73) Assignee: Fraunhofer-Gesellschaft zur Förderung der angewandten Forschung e.V, München (DE)

( * ) Notice: Subject to any disclaimer, the term of this patent is extended or adjusted under 35 U.S.C. 154(b) by 110 days.

(21) Appl. No.: 15/753,541

(22) PCT Filed: Aug. 19, 2016

(86) PCT No.: PCT/EP2016/069680
§ 371 (c)(1),
(2) Date: Feb. 19, 2018

(87) PCT Pub. No.: WO2017/029389
PCT Pub. Date: Feb. 23, 2017

(65) Prior Publication Data
US 2018/0243372 A1 Aug. 30, 2018

(30) Foreign Application Priority Data
Aug. 20, 2015 (EP) .................................... 15181800

(51) Int. Cl.
| | |
|---|---|
| *A61K 38/17* | (2006.01) |
| *A61K 47/68* | (2017.01) |
| *A61K 39/395* | (2006.01) |
| *A61K 45/06* | (2006.01) |
| *A61P 37/00* | (2006.01) |
| *A61P 9/00* | (2006.01) |

(52) U.S. Cl.
CPC ........ *A61K 38/1774* (2013.01); *A61K 39/395* (2013.01); *A61K 45/06* (2013.01); *A61K 47/6811* (2017.08); *A61K 47/6835* (2017.08); *A61P 9/00* (2018.01); *A61P 37/00* (2018.01); *C07K 2319/30* (2013.01)

(58) Field of Classification Search
None
See application file for complete search history.

(56) References Cited

FOREIGN PATENT DOCUMENTS

| | | |
|---|---|---|
| WO | 2014121085 | 8/2014 |
| WO | 2015050663 | 4/2015 |

OTHER PUBLICATIONS

Reynolds et al., (Nephrol Dial Transplant. Apr. 2012;27(4):1343-1350) (Year: 2012).*
Deng et al., (J Immunol. Jan. 15, 2015;194(2):560-574) (Year: 2015).*
Chang et al. Critical Care 2013, 17:R85, (Year: 2013).*
Hotchkiss et al., (The Lancet Infectious Diseases, vol. 13, Issue 3,2013, pp. 260-268) (Year: 2013).*
Zhang et al., "PD-L1 blockade improves survival in experimental sepsis by inhibiting lymphocyte apoptosis and reversing monocyte dysfunction," Critical Care 2010, 14:R220.
Huang et al., "Identification of B7-H1 as a Novel Mediator of the Innate Immune/Proinflammatory Resposne as well as a Possible Myeloid Cell Prognostic Biomarker in Sepsis," J Immunol 2014; 192:1091-1099.
Wang et al., "The effects of PDF-Ig on collagen-induced arthritis," Rheumatol Int (2011) 31:513-519.
Song et al., "Protective effects of Fc-fused PD-L1 on two different animal models of colitis," Gut 2015;64:260-271.
PCT Written Opinion of the ISA PCT/US2016/069680, dated Dec. 9, 2016, EPO, München, DE.
PCT International Search Report PCT/US2016/069680, dated Dec. 9, 2016, EPO, Rijswijk, NL.

* cited by examiner

*Primary Examiner* — Daniel C Gamett
(74) *Attorney, Agent, or Firm* — SAFFIRE IP; Daren P. Nicholson

(57) ABSTRACT

The present invention pertains to a fusion polypeptide for use in treating and/or preventing organ failure in a subject suffering from sepsis, said fusion polypeptide comprises at least (i) a first portion being a Fc portion of an immunoglobulin and (ii) a second portion comprising the extracellular portion of the human B7-H1 polypeptide or a variant thereof. Moreover, also encompassed by the invention is a polynucleotide encoding said fusion polypeptide for use in treating and/or preventing organ failure in a subject suffering from sepsis.

Figure 1:
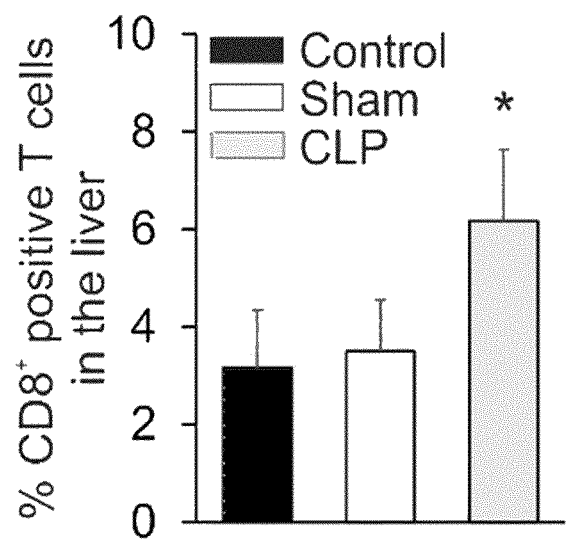

12 Claims, 10 Drawing Sheets
Specification includes a Sequence Listing.

A

B

A

B

A

B

C

D

E

A

B

SEQUENCE LISTING

```
<160> NUMBER OF SEQ ID NOS: 25

<210> SEQ ID NO 1
<211> LENGTH: 663
<212> TYPE: DNA
<213> ORGANISM: Homo sapiens
<220> FEATURE:
<221> NAME/KEY: source
<222> LOCATION: 1..663
<223> OTHER INFORMATION: /mol_type="DNA"
      /organism="Homo sapiens"

<400> SEQUENCE: 1
tttactgtca cggttcccaa ggacctatat gtggtagagt atggtagcaa tatgacaatt      60
gaatgcaaat tcccagtaga aaaacaatta gacctggctg cactaattgt ctattgggaa     120
atggaggata agaacattat tcaatttgtg catggagagg aagacctgaa ggttcagcat     180
agtagctaca gacagagggc ccggctgttg aaggaccagc tctccctggg aaatgctgca     240
cttcagatca cagatgtgaa attgcaggat gcagggtgt accgctgcat gatcagctat     300
ggtggtgccg actacaagcg aattactgtg aaagtcaatg ccccatacaa caaaatcaac     360
caaagaattt tggttgtgga tccagtcacc tctgaacatg aactgacatg tcaggctgag     420
ggctacccca aggccgaagt catctggaca agcagtgacc atcaagtcct gagtggtaag     480
accaccacca ccaattccaa gagagaggag aagcttttca atgtgaccag cacactgaga     540
atcaacacaa caactaatga gattttctac tgcactttta ggagattaga tcctgaggaa     600
aaccatacag ctgaattggt catcccagaa ctacctctgg cacatcctcc aaatgaaagg     660
act                                                                   663

<210> SEQ ID NO 2
<211> LENGTH: 221
<212> TYPE: PRT
<213> ORGANISM: Homo sapiens
<220> FEATURE:
<221> NAME/KEY: SOURCE
<222> LOCATION: 1..221
<223> OTHER INFORMATION: /mol_type="protein"
```

/organism="Homo sapiens"

<400> SEQUENCE: 2

Phe Thr Val Thr Val Pro Lys Asp Leu Tyr Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
            35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
                180                 185                 190

Phe Arg Arg Leu Asp Pro Glu Glu Asn His Thr Ala Glu Leu Val Ile
            195                 200                 205

Pro Glu Leu Pro Leu Ala His Pro Pro Asn Glu Arg Thr
    210                 215                 220

<210> SEQ ID NO 3
<211> LENGTH: 873
<212> TYPE: DNA
<213> ORGANISM: Homo sapiens
<220> FEATURE:
<221> NAME/KEY: source
<222> LOCATION: 1..873
<223> OTHER INFORMATION: /mol_type="DNA"
      /organism="Homo sapiens"

<400> SEQUENCE: 3
atgaggatat ttgctgtctt tatattcatg acctactggc atttgctgaa cgcatttact    60
gtcacggttc ccaaggacct atatgtggta gagtatggta gcaatatgac aattgaatgc   120
aaattcccag tagaaaaaca attagacctg gctgcactaa ttgtctattg ggaaatggag   180
gataagaaca ttattcaatt tgtgcatgga gaggaagacc tgaaggttca gcatagtagc   240
tacagacaga gggcccggct gttgaaggac cagctctccc tgggaaatgc tgcacttcag   300
atcacagatg tgaaattgca ggatgcaggg gtgtaccgct gcatgatcag ctatggtggt   360
gccgactaca agcgaattac tgtgaaagtc aatgccccat acaacaaaat caaccaaaga   420
attttggttg tggatccagt cacctctgaa catgaactga catgtcaggc tgagggctac   480
cccaaggccg aagtcatctg gacaagcagt gaccatcaag tcctgagtgg taagaccacc   540
accaccaatt ccaagagaga ggagaagctt ttcaatgtga ccagcacact gagaatcaac   600

```
acaacaacta atgagatttt ctactgcact tttaggagat tagatcctga ggaaaaccat    660
acagctgaat tggtcatccc agaactacct ctggcacatc ctccaaatga aaggactcac    720
ttggtaattc tgggagccat cttattatgc cttggtgtag cactgacatt catcttccgt    780
ttaagaaaag ggagaatgat ggatgtgaaa aatgtggca tccaagatac aaactcaaag    840
aagcaaagtg atacacattt ggaggagacg taa                                 873
```

<210> SEQ ID NO 4
<211> LENGTH: 290
<212> TYPE: PRT
<213> ORGANISM: Homo sapiens
<220> FEATURE:
<221> NAME/KEY: SOURCE
<222> LOCATION: 1..290
<223> OTHER INFORMATION: /mol_type="protein"
      /organism="Homo sapiens"

<400> SEQUENCE: 4

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
290
```

<210> SEQ ID NO 5
<211> LENGTH: 663
<212> TYPE: DNA
<213> ORGANISM: Mus musculus
<220> FEATURE:
<221> NAME/KEY: source
<222> LOCATION: 1..663
<223> OTHER INFORMATION: /mol_type="DNA"
      /organism="Mus musculus"

<400> SEQUENCE: 5

```
tttactatca cggctccaaa ggacttgtac gtggtggagt atggcagcaa cgtcacgatg    60
gagtgcagat tccctgtaga acgggagctg gacctgcttg cgttagtggt gtactgggaa   120
aaggaagatg agcaagtgat tcagtttgtg gcaggagagg aggaccttaa gcctcagcac   180
agcaacttca gggggagagc ctcgctgcca aaggaccagc ttttgaaggg aaatgctgcc   240
cttcagatca cagacgtcaa gctgcaggac gcaggcgttt actgctgcat aatcagctac   300
ggtggtgcgg actacaagcg aatcacgctg aaagtcaatg ccccataccg caaaatcaac   360
cagagaattt ccgtggatcc agccacttct gagcatgaac taatatgtca ggccgagggt   420
tatccagaag ctgaggtaat ctggacaaac agtgaccacc aacccgtgag tgggaagaga   480
agtgtcacca cttcccggac agaggggatg cttctcaatg tgaccagcag tctgagggtc   540
aacgccacag cgaatgatgt tttctactgt acgttttgga gatcacagcc agggcaaaac   600
cacacagcgg agctgatcat cccagaactg cctgcaacac atcctccaca gaacaggact   660
cac                                                                 663
```

<210> SEQ ID NO 6
<211> LENGTH: 221
<212> TYPE: PRT
<213> ORGANISM: Mus musculus
<220> FEATURE:
<221> NAME/KEY: SOURCE
<222> LOCATION: 1..221
<223> OTHER INFORMATION: /mol_type="protein"
      /organism="Mus musculus"

<400> SEQUENCE: 6

Phe Thr Ile Thr Ala Pro Lys Asp Leu Tyr Val Val Glu Tyr Gly Ser
1               5                   10                  15

Asn Val Thr Met Glu Cys Arg Phe Pro Val Glu Arg Glu Leu Asp Leu
                20                  25                  30

Leu Ala Leu Val Val Tyr Trp Glu Lys Glu Asp Glu Gln Val Ile Gln
            35                  40                  45

Phe Val Ala Gly Glu Glu Asp Leu Lys Pro Gln His Ser Asn Phe Arg
        50                  55                  60

Gly Arg Ala Ser Leu Pro Lys Asp Gln Leu Leu Lys Gly Asn Ala Ala
65                  70                  75                  80

Leu Gln Ile Thr Asp Val Lys Leu Gln Asp Ala Gly Val Tyr Cys Cys
                85                  90                  95

Ile Ile Ser Tyr Gly Gly Ala Asp Tyr Lys Arg Ile Thr Leu Lys Val
            100                 105                 110

Asn Ala Pro Tyr Arg Lys Ile Asn Gln Arg Ile Ser Val Asp Pro Ala
        115                 120                 125

Thr Ser Glu His Glu Leu Ile Cys Gln Ala Glu Gly Tyr Pro Glu Ala
    130                 135                 140

Glu Val Ile Trp Thr Asn Ser Asp His Gln Pro Val Ser Gly Lys Arg

```
                    145                 150                 155                 160
Ser  Val  Thr  Thr  Ser  Arg  Thr  Glu  Gly  Met  Leu  Leu  Asn  Val  Thr  Ser
                    165                 170                 175

Ser  Leu  Arg  Val  Asn  Ala  Thr  Ala  Asn  Asp  Val  Phe  Tyr  Cys  Thr  Phe
                    180                 185                 190

Trp  Arg  Ser  Gln  Pro  Gly  Gln  Asn  His  Thr  Ala  Glu  Leu  Ile  Ile  Pro
               195                 200                 205

Glu  Leu  Pro  Ala  Thr  His  Pro  Pro  Gln  Asn  Arg  Thr  His
          210                 215                 220
```

<210> SEQ ID NO 7
<211> LENGTH: 873
<212> TYPE: DNA
<213> ORGANISM: Mus musculus
<220> FEATURE:
<221> NAME/KEY: source
<222> LOCATION: 1..873
<223> OTHER INFORMATION: /mol_type="DNA"
      /organism="Mus musculus"

<400> SEQUENCE: 7

```
atgaggatat tgctggcat tatattcaca gcctgctgtc acttgctacg ggcgtttact       60
atcacggctc caaaggactt gtacgtggtg gagtatggca gcaacgtcac gatggagtgc      120
agattccctg tagaacggga gctggacctg cttgcgttag tggtgtactg ggaaaaggaa      180
gatgagcaag tgattcagtt tgtggcagga gaggaggacc ttaagcctca gcacagcaac      240
ttcagggga gagcctcgct gccaaaggac cagcttttga agggaaatgc tgcccttcag       300
atcacagacg tcaagctgca ggacgcaggc gtttactgct gcataatcag ctacggtggt      360
gcggactaca gcgaatcac gctgaaagtc aatgccccat accgcaaaat caaccagaga      420
atttccgtgg atccagccac ttctgagcat gaactaatat gtcaggccga gggttatcca      480
gaagctgagg taatctggac aaacagtgac caccaacccg tgagtgggaa gagaagtgtc      540
accacttccc ggacagaggg gatgcttctc aatgtgacca gcagtctgag ggtcaacgcc      600
acagcgaatg atgttttcta ctgtacgttt tggagatcac agccagggca aaaccacaca      660
gcggagctga tcatcccaga actgcctgca acacatcctc cacagaacag gactcactgg      720
gtgcttctgg gatccatcct gttgttcctc attgtagtgt ccacggtcct cctcttcttg      780
agaaaacaag tgagaatgct agatgtggag aaatgtggcg ttgaagatac aagctcaaaa      840
aaccgaaatg atacacaatt cgaggagacg taa                                   873
```

<210> SEQ ID NO 8
<211> LENGTH: 290
<212> TYPE: PRT
<213> ORGANISM: Mus musculus
<220> FEATURE:
<221> NAME/KEY: SOURCE
<222> LOCATION: 1..290
<223> OTHER INFORMATION: /mol_type="protein"
      /organism="Mus musculus"

<400> SEQUENCE: 8

```
Met  Arg  Ile  Phe  Ala  Gly  Ile  Ile  Phe  Thr  Ala  Cys  Cys  His  Leu  Leu
1                   5                   10                  15

Arg  Ala  Phe  Thr  Ile  Thr  Ala  Pro  Lys  Asp  Leu  Tyr  Val  Val  Glu  Tyr
                    20                  25                  30

Gly  Ser  Asn  Val  Thr  Met  Glu  Cys  Arg  Phe  Pro  Val  Glu  Arg  Glu  Leu
               35                  40                  45
```

```
Asp Leu Leu Ala Leu Val Val Tyr Trp Glu Lys Glu Asp Glu Gln Val
 50                  55                  60

Ile Gln Phe Val Ala Gly Glu Glu Asp Leu Lys Pro Gln His Ser Asn
 65                  70                  75                  80

Phe Arg Gly Arg Ala Ser Leu Pro Lys Asp Gln Leu Leu Lys Gly Asn
                 85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
        115                 120                 125

Lys Val Asn Ala Pro Tyr Arg Lys Ile Asn Gln Arg Ile Ser Val Asp
130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
        195                 200                 205

Thr Phe Trp Arg Ser Gln Pro Gly Gln Asn His Thr Ala Glu Leu Ile
210                 215                 220

Ile Pro Glu Leu Pro Ala Thr His Pro Pro Gln Asn Arg Thr His Trp
225                 230                 235                 240

Val Leu Leu Gly Ser Ile Leu Leu Phe Leu Ile Val Val Ser Thr Val
                245                 250                 255

Leu Leu Phe Leu Arg Lys Gln Val Arg Met Leu Asp Val Glu Lys Cys
            260                 265                 270

Gly Val Glu Asp Thr Ser Ser Lys Asn Arg Asn Asp Thr Gln Phe Glu
        275                 280                 285

Glu Thr
290

<210> SEQ ID NO 9
<211> LENGTH: 459
<212> TYPE: PRT
<213> ORGANISM: Homo sapiens
<220> FEATURE:
<221> NAME/KEY: SOURCE
<222> LOCATION: 1..459
<223> OTHER INFORMATION: /mol_type="protein"
      /note="B7-H1 (Phe19-Thr239)-Linker(DIEGRMD)-IgG1(Pro100-Lys330)"
      /organism="Homo sapiens"

<400> SEQUENCE: 9

Phe Thr Val Thr Val Pro Lys Asp Leu Tyr Val Val Glu Tyr Gly Ser
 1               5                  10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
 65                  70                  75                  80

Leu Gln Ile Thr Asp Val Lys Leu Gln Asp Ala Gly Val Tyr Arg Cys
                 85                  90                  95
```

```
Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Gly Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Thr Asp Ile Glu
    210                 215                 220

Gly Arg Met Asp Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
    290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Asp
        355                 360                 365

Glu Leu Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro Gly Lys
    450                 455

<210> SEQ ID NO 10
<211> LENGTH: 45
<212> TYPE: DNA
<213> ORGANISM: Mus musculus
<220> FEATURE:
<221> NAME/KEY: source
<222> LOCATION: 1..45
<223> OTHER INFORMATION: /mol_type="DNA"
```

```
              /note="forward primer"
              /organism="Mus musculus"

<400> SEQUENCE: 10
cgcccggggg ggatcatgag gatatttgct ggcattatat tcaca            45

<210> SEQ ID NO 11
<211> LENGTH: 35
<212> TYPE: DNA
<213> ORGANISM: Mus musculus
<220> FEATURE:
<221> NAME/KEY: source
<222> LOCATION: 1..35
<223> OTHER INFORMATION: /mol_type="DNA"
      /note="reverse primer"
      /organism="Mus musculus"

<400> SEQUENCE: 11
tcaagcttgc atgccttact tgtacagctc gtcca                       35

<210> SEQ ID NO 12
<211> LENGTH: 53
<212> TYPE: DNA
<213> ORGANISM: Mus musculus
<220> FEATURE:
<221> NAME/KEY: source
<222> LOCATION: 1..53
<223> OTHER INFORMATION: /mol_type="DNA"
      /note="forward primer for cloning"
      /organism="Mus musculus"

<400> SEQUENCE: 12
gatccgctag agatcgccac catgaggata tttgctggca ttatattcac agc   53

<210> SEQ ID NO 13
<211> LENGTH: 39
<212> TYPE: DNA
<213> ORGANISM: Mus musculus
<220> FEATURE:
<221> NAME/KEY: source
<222> LOCATION: 1..39
<223> OTHER INFORMATION: /mol_type="DNA"
      /note="reverse primer for cloning"
      /organism="Mus musculus"

<400> SEQUENCE: 13
tccggtggat cggatttact tgtacagctc gtccatgcc                   39

<210> SEQ ID NO 14
<211> LENGTH: 20
<212> TYPE: DNA
<213> ORGANISM: Homo sapiens
<220> FEATURE:
<221> NAME/KEY: source
<222> LOCATION: 1..20
<223> OTHER INFORMATION: /mol_type="DNA"
      /note="qPCR primer B7-H1 forward"
      /organism="Homo sapiens"

<400> SEQUENCE: 14
tgcagcagta aacgcctgcg                                        20

<210> SEQ ID NO 15
<211> LENGTH: 20
<212> TYPE: DNA
<213> ORGANISM: Homo sapiens
<220> FEATURE:
<221> NAME/KEY: source
<222> LOCATION: 1..20
```

<223> OTHER INFORMATION: /mol_type="DNA"
    /note="qPCR primer B7-H1 reverse"
    /organism="Homo sapiens"

<400> SEQUENCE: 15
cgctgccaaa ggaccagctt                                               20

<210> SEQ ID NO 16
<211> LENGTH: 20
<212> TYPE: DNA
<213> ORGANISM: Homo sapiens
<220> FEATURE:
<221> NAME/KEY: source
<222> LOCATION: 1..20
<223> OTHER INFORMATION: /mol_type="DNA"
    /note="qPCR primer IL-2 forward"
    /organism="Homo sapiens"

<400> SEQUENCE: 16
tgagcatcct ggggagtttc                                               20

<210> SEQ ID NO 17
<211> LENGTH: 20
<212> TYPE: DNA
<213> ORGANISM: Homo sapiens
<220> FEATURE:
<221> NAME/KEY: source
<222> LOCATION: 1..20
<223> OTHER INFORMATION: /mol_type="DNA"
    /note="qPCR primer IL-2 reverse "
    /organism="Homo sapiens"

<400> SEQUENCE: 17
gtgacctcaa gtcctgcagg                                               20

<210> SEQ ID NO 18
<211> LENGTH: 18
<212> TYPE: DNA
<213> ORGANISM: Homo sapiens
<220> FEATURE:
<221> NAME/KEY: source
<222> LOCATION: 1..18
<223> OTHER INFORMATION: /mol_type="DNA"
    /note="qPCR primer Fas-L forward"
    /organism="Homo sapiens"

<400> SEQUENCE: 18
accaaccaaa gccttaaa                                                 18

<210> SEQ ID NO 19
<211> LENGTH: 18
<212> TYPE: DNA
<213> ORGANISM: Homo sapiens
<220> FEATURE:
<221> NAME/KEY: source
<222> LOCATION: 1..18
<223> OTHER INFORMATION: /mol_type="DNA"
    /note="qPCR primer Fas-L reverse"
    /organism="Homo sapiens"

<400> SEQUENCE: 19
atacttcact ccagagat                                                 18

<210> SEQ ID NO 20
<211> LENGTH: 20
<212> TYPE: DNA
<213> ORGANISM: Homo sapiens
<220> FEATURE:
<221> NAME/KEY: source

```
<222> LOCATION: 1..20
<223> OTHER INFORMATION: /mol_type="DNA"
      /note="qPCR primer granzyme B forward"
      /organism="Homo sapiens"

<400> SEQUENCE: 20
ctccacgtgc tttcaccaaa                                               20

<210> SEQ ID NO 21
<211> LENGTH: 21
<212> TYPE: DNA
<213> ORGANISM: Homo sapiens
<220> FEATURE:
<221> NAME/KEY: source
<222> LOCATION: 1..21
<223> OTHER INFORMATION: /mol_type="DNA"
      /note="qPCR Primer granzyme B reverse"
      /organism="Homo sapiens"

<400> SEQUENCE: 21
ggaaaatagt acagagaggc a                                             21

<210> SEQ ID NO 22
<211> LENGTH: 21
<212> TYPE: DNA
<213> ORGANISM: Homo sapiens
<220> FEATURE:
<221> NAME/KEY: source
<222> LOCATION: 1..21
<223> OTHER INFORMATION: /mol_type="DNA"
      /note="qPCR primer perforin forward"
      /organism="Homo sapiens"

<400> SEQUENCE: 22
tgctacactg ccactcggtc a                                             21

<210> SEQ ID NO 23
<211> LENGTH: 21
<212> TYPE: DNA
<213> ORGANISM: Homo sapiens
<220> FEATURE:
<221> NAME/KEY: source
<222> LOCATION: 1..21
<223> OTHER INFORMATION: /mol_type="DNA"
      /note="qPCR primer perforin reverse"
      /organism="Homo sapiens"

<400> SEQUENCE: 23
ttggctacct tggagtggga g                                             21

<210> SEQ ID NO 24
<211> LENGTH: 20
<212> TYPE: DNA
<213> ORGANISM: Homo sapiens
<220> FEATURE:
<221> NAME/KEY: source
<222> LOCATION: 1..20
<223> OTHER INFORMATION: /mol_type="DNA"
      /note="qPCR primer IFNγ forward "
      /organism="Homo sapiens"

<400> SEQUENCE: 24
tttgcagctc ttcctcatgg                                               20

<210> SEQ ID NO 25
<211> LENGTH: 20
<212> TYPE: DNA
<213> ORGANISM: Homo sapiens
<220> FEATURE:
```

```
<221> NAME/KEY: source
<222> LOCATION: 1..20
<223> OTHER INFORMATION: /mol_type="DNA"
      /note="qPCR primer IFNγ reverse"
      /organism="Homo sapiens"

<400> SEQUENCE: 25
tcgccttgct gttgctgaag                                              20
```

B7-H1 FUSION POLYPEPTIDES FOR TREATING AND PREVENTING ORGAN FAILURE

The present invention pertains to a fusion polypeptide for use in treating and/or preventing organ failure in a subject suffering from sepsis, said fusion polypeptide comprises at least (i) a first portion being an Fc portion of an immunoglobulin and (ii) a second portion comprising the extracellular portion of the human B7-H1 polypeptide or a variant thereof. Moreover, also encompassed by the invention is a polynucleotide encoding said fusion polypeptide for use in treating and/or preventing organ failure in a subject suffering from sepsis. Sepsis is a life-threatening illness that can occur when the whole body reacts to an infection.

Despite intensive research, sepsis remains the third leading cause of mortality in intensive care units (Balk, 2004; Dellinger et al., 2008; Kaukonen et al., 2014; Vincent et al., 2014). Pathophysiologically, during sepsis progression there is an initial hyper-inflammatory phase which provokes the onset of a hypo-inflammatory stage, partly occurring in parallel (Angus and van der Poll, 2013; Munford and Pugin, 2001; Vincent et al., 2013).

Recent therapy approaches mainly focus on the treatment of the hyper-inflammatory response to confine the release of pro-inflammatory mediators, block their function, or remove them from the circulation. One most promising candidate, inhibition of which was shown to significantly improve sepsis survival in a rodent model, was TNFα (Marquez-Velasco et al., 2006). Using neutralizing antibodies, this approach was translated into the human situation, but failed to improve sepsis survival (Clark et al., 1998; Reinbart et al., 2001). However, with this approach, the hyper-inflammation is limited and most patients survive this phase. Because blocking the pro-inflammatory immune response reduces the host's ability to fight and control primary and secondary infections, this therapy approach finally failed to significantly improve sepsis survival, but caused or enhanced the hypo-inflammatory phase. This immunosuppression often provokes multi-organ-dysfunction syndrome (MODS) and the patient's death (Otto et al., 2011; Torgersen et al., 2009).

Treatment approaches to rescue the patient during immune paralysis have also been applied. Taking into consideration that monocytes are deactivated (Docke et al., 1997; Pangault et al., 2006), GM-CSF treatment restored monocyte function during sepsis (Meisel et al., 2009). In the mouse model, antagonizing the nuclear receptor peroxisome proliferator-activated receptor γ (PPARγ) has been shown to avert T cell depletion (Schmidt et al., 2011), one hallmark of immune paralysis associated with the hyper-inflammatory phase, correlating with sepsis mortality (Hotchkiss et al., 2006; Wesche-Soldato et al., 2007b). Due to the multi causal origin of sepsis, the various pre-existing co-morbidities, or genetic preconditions of the patients, an appropriate patient specific treatment is still difficult to achieve (Hotchkiss and Karl, 2003; Hotchkiss and Opal, 2010).

In general, disease severity is already far advanced when sepsis is diagnosed in the patient and liver damage, a relatively late event during sepsis progression, has already occurred. During sepsis, organ failure, often followed by a multi-organ-dysfunction syndrome (MODS), frequently results in the patient's death. Therefore, understanding mechanisms leading to organ damage are mandatory to improve already existing care options or to set up new therapy approaches.

Thus, there is a strong need for treatment and/or prevention of organ failure during sepsis.

The technical problem underlying the present invention can be seen as the provision of means and methods for complying with the aforementioned needs. The technical problem is solved by the embodiments characterized in the claims and herein below.

Therefore, the present invention relates to a fusion polypeptide for use in treating and/or preventing organ failure in a subject suffering from sepsis, said fusion polypeptide comprises at least (i) a first portion being a Fc portion of an immunoglobulin and (ii) a second portion comprising the extracellular portion of the human B7-H1 polypeptide or a variant thereof.

The term "polypeptide" as used herein refers to a molecule consisting of several, typically, at least 20, at least 30, at least 40, at least 50 or at least 60 amino acids that are covalently linked to each other by peptide bonds. Molecules consisting less than 20 amino acids covalently linked by peptide bonds are usually considered to be peptides.

A "fusion polypeptide" in accordance with the present invention refers to a polypeptide that is composed of at least two polypeptides or peptides. Thus, it will be understood that a fusion polypeptide as referred to herein may comprise two, three, four, five or even more polypeptide or peptide portions. However, in accordance with the present invention, the fusion polypeptide shall comprise at least a first and a second portion as specified herein. The polypeptide or peptide portions comprised in the fusion polypeptide may be linked to each other either permanently, typically by peptide bonds, or reversibly, e.g., via disulfide bonds or affinity binding based on ionic bonds, hydrogen bonds and/or van der Waals forces. Permanent binding between the portions of the fusion polypeptide according to the present invention can be achieved typically by recombinant manufacture. To this end, a polynucleotide encoding the said portions is synthesized either chemically or by recombinant DNA techniques and expressed in a suitable expression system. Afterwards, the expressed fusion polypeptide can be purified from the expression system. Various affinity binding systems comprising a ligand and a receptor portion are known in the art such that the skilled artisan can be used in order to construe fusion polypeptides comprising the different peptide or polypeptide portions reversibly bound to each other without further ado. Typical examples of such affinity binding systems are those based on antibodies/antigens, streptavidin/biotin, avidin/biotin, and others well known in the art.

The fusion polypeptide applied in accordance with the present invention shall comprise a first portion being an Fc portion of an immunoglobulin and a second portion comprising the extracellular portion of the human B7-H1 polypeptide or a variant thereof. Preferably, the extracellular portion of the human B7-H1 polypeptide or a variant thereof is located N-terminally in the fusion polypeptide while the Fc portion of the immunoglobulin is located C-terminally.

The term "Fragment crystallizable (Fc) portion of an immunoglobulin" refers to antibody fragments which comprise the $C_H2$ and $C_H3$ domains of an antibody and which can be obtained by proteolytic cleavage of an antibody using, e.g., papain. Various immunoglobulins are known in the art from a variety of different species. These immunoglobulins encompass IgA, IgD, IgE, IgG, IgM, IgW or IgY. Preferred in accordance with the present invention among the immunoglobulins are, however, those which appear in mammals and, in particular, in humans, i.e. IgA, IgD, IgE, IgG, IgM. The Fc portion of an antibody determines the class effect. Since only the constant domains of the heavy chains form the Fc portion of an antibody, the classes of the heavy chains determine the class effects. Possible classes of heavy chains in antibodies encompass alpha, gamma, delta, epsilon, and mu. These heavy chain classes define the isotype. Different isotypes of antibodies have different class effects due to their respective Fc portions. Such Fc mediated class effects include those affecting effector cells or effector molecules, e.g., opsonisation, agglutination, haemolysis, complement activation, and mast cell degranulation. Amino acid sequences for $C_H2$ and $C_H3$ domains forming the Fc portions are well known in the art for different antibody isotypes and can be provided by the skilled artisan without further ado. The Fc portion as referred to in accordance with the present invention may be, preferably, posttranslationally modified and, more preferably, glycosylated. Preferably, said immunoglobulin in accordance with the present invention is IgG and, more preferably, human IgG. Amino acid sequences encoding human IgG are well known in the art as well as the nucleic acid sequences encoding them. Moreover, it is also well known which amino acids correspond to the Fc portions in the said amino acid sequences.

The term "extracellular portion of the human B7-H1 polypeptide" refers to the extracellular part of the human B7 homolog1 protein also known as Programmed death-ligand 1 (PD-L1) or Cluster of differentiation 274 (CD274). The B7-H1 protein is a 40 kDa transmembrane protein known to bind to the PD-1 receptor found on activated T cells. The B7-H1/PD-1 complex has been suggested to be involved in the control of the proliferation of CD8+ T cells. Amino acid sequences for the human B7-H1 protein are well known in the art.

Preferably, an amino acid sequence for human B7-H1 to be used in accordance with the present invention is publicly available under UniprotKB No: Q9NZQ7, is shown in SEQ ID NO: 4 or is encoded by the nucleic acid sequence shown in SEQ ID NO: 3 or under GenBank Accession number AF177937. The extracellular portion of the said human B7-H1 encompasses the amino acids 19 to 239 of the sequence publicly available under UniprotKB No: Q9NZQ7, is shown in SEQ ID NO: 2, is encoded by the nucleic acid sequence shown in SEQ ID NO: 1 or is encoded by nucleotides 55 to 717 of the sequence under GenBank Accession number AF177937.

Preferably, an amino acid sequence for murine B7-H1 to be used in accordance with the present invention is publicly available under UniprotKB No: Q9EP73, is shown in SEQ ID NO: 8 or is encoded by the nucleic acid sequence shown in SEQ ID NO: 7 or under GenBank Accession number NM_021893. The extracellular portion of the said murine B7-H1 encompasses the amino acids 19 to 239 of the sequence publicly available under UniprotKB No: Q9EP73, is shown in SEQ ID NO: 6, is encoded by the nucleic acid sequence shown in SEQ ID NO: 5 or is encoded by nucleotides 55 to 717 of the sequence under GenBank Accession number NM_021893.

Encompassed as extracellular portions of the human B7-H1 polypeptide according to the present invention are, preferably, variants of any of the aforementioned specific extracellular domains. Such a variant, typically, differs from the specific amino acid sequences referred to before by at least one amino acid substitution, deletion and/or addition. Nevertheless, the variant of the extracellular portion of the human B7-H1 polypeptide shall still be capable of exerting the biological effects mediated by the extracellular portion of the human B7-H1 polypeptide and, in particular, remaining capable of binding to PD-1. Said variant shall, preferably, have an amino acid sequence which is at least 70%, at least 75%, at least 80%, at least 85%, at least 90%, at least 95%, at least 96%, at least 97%, at least 98% or at least 99% identical to the amino acid sequence shown in SEQ ID NO: 2 or 6 or to an amino acid sequence encoded by the nucleic acid sequences shown in SEQ ID NO: 1 or 5. Sequence identity between amino acid sequences or nucleic acid sequences as used herein can be assessed by determining the number of identical nucleotides or amino acids between two nucleic acid sequences or amino acid sequences wherein the sequences are aligned so that the highest order match is obtained. It can be calculated using published techniques or methods codified in computer programs such as, for example, BLASTP, BLASTN or FASTA (Altschul 1990, J Mol Biol 215, 403). The percent identity values are, preferably, calculated over a comparison window. A comparison window, preferably, is the length of the entire sequence of the shorter sequence to be aligned or at least half of said sequence. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (Higgins 1989, CABIOS 5, 151) or the programs Gap and BestFit (Needleman 1970, J Mol Biol 48: 443; Smith 1981, Adv Appl Math 2: 482), which are part of the GCG software packet (Genetics Computer Group 1991, 575 Science Drive, Madison, Wis., USA 53711), may be used. The sequence identity values recited above in percent (%) are to be determined, in another aspect of the invention, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

Also encompassed by the invention as variants of the aforementioned specific extracellular portions of the human B7-H1 polypeptide are those which are encoded by polynucleotides having a nucleic acid sequence which is capable of hybridizing to the nucleic acid sequences encoding the aforementioned specific extracellular portions of the human or murine B7-H1 polypeptide under stringent hybridization conditions. Stringent hybridization conditions as used herein are those which allow for identifying polynucleotides encoding polypeptides which have essentially the same biological function as B7-H1. Preferably, stringent hybridization conditions in accordance with the present invention are: hybridization in 6× sodium chloride/sodium citrate (SSC) at 45° C., followed by one or more wash steps in 0.2×SSC, 0.1% SDS at a temperature between 50° C. to 65° C. The skilled worker knows that these hybridization conditions differ depending on the type of nucleic acid and, for example, when organic solvents are present, with regard to the temperature and concentration of the buffer. Details on nucleic acid hybridization techniques are well known to those skilled in the art and can be found in standard text books such as Sambrook et al. Alternatively, polynucleotide encoding the aforementioned variants can also be obtained by PCR-based techniques such as mixed oligonucleotide primer-based amplification of DNA, i.e. using degenerated primers against conserved domains of the extracellular portions of the human or murine B7-H1 polypeptide. Conserved domains may be identified by a sequence comparison of the amino acid or nucleic acid sequences of the extracellular portion of human or murine B7-H1.

Preferably, the aforementioned variants of the extracellular portion of the human B7-H1 polypeptide comprise at least one of the following amino acid exchanges L27A, S34Y, D49S, Y56S, E58S, K62S, H69F, E72S, K75S, K89S, A98F, Q100S, R113Y, and S117Y. These aforementioned amino acid exchanges in the extracellular portion of the human B7-H1 polypeptide correspond to the following amino acid exchanges in the extracellular portion of the murine B7-H1 polypeptide: L27A, S34Y, D49S, Y56S, E58S, E62S, A69F, E72S, K75S, K89S, A98F, Q100S, C113Y, and S117Y. These amino acid exchanges have been previously reported to enhance binding and/or activity of B7-H1 protein to PD-1; see Wang 2003, J. Exp. Med. 197 No. 9: 1083-1091.

Also preferably, the fusion polypeptide to be applied in accordance with the present invention has an amino acid sequence as shown in SEQ ID NO: 9 or is a variant thereof which has at least one at least one amino acid substitution, deletion and/or addition. The said variant fusion protein shall still be capable of exerting the biological effects mediated by the extracellular portion of the human B7-H1 polypeptide and, in particular, remaining capable of binding to PD-1. Said variant shall, preferably, have an amino acid sequence which is at least at least 70%, at least 75%, at least 80%, at least 85%, at least 90%, at least 95%, at least 96%, at least 97%, at least 98% or at least 99% identical to the amino acid sequence shown in SEQ ID NO: 9.

The fusion polypeptide according to the present invention may also comprise further portions such as linker or spacer sequences between the individual portions. Moreover, also encompassed are portions contributing further functions. Such portions include, e.g., portions which allow for targeting of certain cells in an organism, portions which increase stability of the fusion polypeptide as well as portions which facilitate manufacture and/or purification of the fusion polypeptide such as tags.

Preferably the said fusion polypeptide comprises a third portion for targeting and, in particular, a third portion being a polypeptide capable of binding specifically to cytotoxic T-cells. More preferably, said polypeptide capable of binding specifically to cytotoxic T-cells is selected from the group consisting of: a polypeptide comprising a portion of the MHC-I complex which is capable of binding to CD8, a portion of the CD80 which is capable of binding to CD28, a polypeptide being an antibody or fragment thereof capable of specifically binding to CD8, a polypeptide being an antibody or fragment thereof capable of specifically binding to CD28, and CD2-binding portion of lymphocyte function associated antigen-3 (LFA-3). How such portions can be derived from the respective proteins is well known to the person skilled in the art.

The term "treating" as used herein refers to ameliorating or curing a disease or at least one symptom associated therewith. Thus, if there is amelioration or cure of the disease or at least a symptom associated therewith, the treatment shall be deemed to be effective. It will be understood that treating might not be effective in all subjects. However, according to the present invention it is envisaged that treatment will be effective in at least a statistically significant portion of subjects to be treated. It is well known to the skilled artisan how to determine a statistically significant portion of subjects that can be effectively treated. Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. Preferably, the probability envisaged by the present invention allows that the finding of effective treatment will be correct for at least 60%, at least 70%, at least 80%, or at least 90% of the subjects of a given cohort or population.

The term "preventing" as used herein refers to avoiding the onset of the disease or at least one symptom associated therewith or to prevent the worsening of the disease or the said at least one symptom. The prevention as referred to herein can be typically achieved either for the period during which a drug is administered. If the administration of the drug is stopped, however, the prevention may not persist for an unlimited time but may remain present for a certain preventive time window after application of the drug. Typically, a preventive time window in accordance with the present invention may be at least 1 day, at least 2 days, at least 3 days, at least 4 days, at least 5 days, at least 6 days, or at least 7 days. However, the preventive time window may also depend on the dosage of a drug as well as the mode of administration or the kind of formulation. For example, if a high dosage is applied, usually longer preventive time windows can be achieved. The same holds true if slow release formulations of a drug are administered or the drug is administered via routes that do not lead to immediate metabolization of a drug in the subject. In such cases, the predictive time window may be increased up to several weeks, months or even years. It will be understood that prevention might not be effective in all subjects. However, according to the present invention it is envisaged that prevention will be effective in at least a statistically significant portion of subjects. It is well known to the skilled artisan how to determine a statistically significant portion of subjects that can be effectively prevented. Whether a portion is statistically significant can be determined without further ado by the person skilled in the art using various well known statistic evaluation tools as discussed above.

Since the fusion polypeptide according to the present invention shall be used for treating and/or preventing organ failure, it shall, preferably, be formulated as a medicament. A medicament in the sense of the present invention refers, preferably, to a pharmaceutical composition containing the biologically active fusion polypeptide according to the invention as pharmaceutical active compound and one or more other components such as one or more pharmaceutically acceptable carrier(s).

The fusion polypeptide can be present in liquid or lyophilized form. For example, the fusion polypeptide can be present together with glycerol and/or protein stabilizers (e.g., human serum albumin).

The medicament is, typically, administered systemically and, preferably, intravenously or intramuscularly. However, depending on the nature of the formulation and the desired therapeutic application, the medicament may be administered by other routes as well.

The fusion polypeptide is the active ingredient or drug of the medicament, and is preferably administered in conventional dosage forms prepared by combining the drug with standard pharmaceutical carriers according to conventional procedures. These procedures may involve mixing, granulating, and compression, or dissolving the ingredients as appropriate to the desired preparation. It will be appreciated that the form and character of the pharmaceutical acceptable carrier or diluent is dictated by the amount of active ingredient with which it is to be combined, the route of administration, and other well-known variables.

The carrier(s) must be acceptable in the sense of being compatible with the other ingredients of the formulation and being not deleterious to the recipient thereof. The pharmaceutical carrier employed may include a solid, a gel, or a liquid. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil, water, emulsions, various types of wetting agents, and the like. Similarly, the carrier or diluent may include time delay material well known to the art, such as glyceryl mono-stearate or glyceryl distearate alone or with a wax. Said suitable carriers comprise those mentioned above and others well known in the art, see, e.g., Remington's Pharmaceutical Sciences, Mack Publishing Company, Easton, Pa.

The diluent(s) is/are selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or non-toxic, non-therapeutic, non-immunogenic stabilizers and the like.

A therapeutically effective dose refers to an amount of the fusion polypeptide according to the invention to be used in medicament which prevents, ameliorates or cures the symptoms accompanying a disease or condition referred to in this specification. Therapeutic efficacy and toxicity of a drug can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. The dosage regimen will be determined by the attending physician and by clinical factors. As is well known in the medical arts, dosages for any one patient depends upon many factors, including the patient's size, age, the particular formulation of the medicament to be administered, sex, time and route of administration, general health, and other drugs being administered concurrently. Progress can be monitored by periodic assessment. Dosage recommendations shall be indicated in the prescribers or users instructions in order to anticipate dose adjustments depending on the considered recipient.

The medicament referred to herein is, preferably, administered at least once, e.g. as a bolus. However, the said medicament may be administered more than one time and, preferably, at least twice, e.g. permanently or periodically after defined time windows.

The medicament according to the present invention may in a further aspect of the invention comprise drugs in addition to the fusion polypeptide which are added during its formulation. Preferably, the fusion polypeptide according to the invention is to be applied together with at least one further drug and, thus, may be formulated together with these other drugs as a medicament. More preferably, said at least one further drug is selected from the group consisting of: antibiotics, vasopressors, steroids, anticoagulants, anti-thrombotics, proinflammatory cytokines and DAMP inhibitors.

Finally, it is to be understood that the formulation of a pharmaceutical composition takes place under GMP standardized conditions or the like in order to ensure quality, pharmaceutical security, and effectiveness of the medicament.

The term "organ failure" as used herein refers to any dysfunction of the organ which affects the physiologically expected function of an organ to such an extent that normal homeostasis can neither be maintained nor endogenously compensated. Organ failure may be acute or chronic. Symptoms associated with organ failure depend on the affected organ usually become apparent by a pathological physiology in the subject which can be determined, e.g., by clinical or biochemical parameters. Symptoms of organ failure are also well known in the art and are described in medicinal text books. Preferably, organ failure as referred to herein is multi organ failure. Multi organ failure is characterized by the failure of two or more organs at the same time or sequentially within a short period of time. It can be often observed as a consequence of severe infections or inflammatory reactions such as systemic inflammatory response syndrome (SIRS) or sepsis. Typical organs which fail during SIRS or sepsis are lung, kidney, heart and/or the entire circulation system, the gastrointestinal system as well as the nervous system. Preferably, the multi organ failure referred to herein is caused by autoreactive cytotoxic cells and, more preferably, is CD8 cytotoxic T-cell dependent multi-organ failure.

The term "subject" as used herein refers to any kind of animal encompassing, e.g., mammals, birds, fish or reptiles. Typically, the said animal, however, is a mammal such as a mammals used as pets including dogs, cats, horses, or rodents, laboratory animals, e.g., rats, mice or apes, or farming animals such as pigs, cows, goats, or sheep. More preferably, the mammal is a primate and, most preferably, a human. The subject according to the present invention shall suffer from sepsis, i.e. it shall exhibit at least one or more pathological changes such as clinically apparent symptoms or changes of physiological or molecular parameters which are typically associated with sepsis.

The term "sepsis" as used herein refers to an inflammatory response affecting the entire organism. Typical symptoms associated with sepsis are well known in the art and described in standard textbooks of medicine. They include a significantly altered body temperature (low temperature or fever), rapid breathing, tachycardia, low blood pressure due to decreased peripheral vascular resistance, mental confusion and edema formation. Biochemical parameters such as coagulation dysfunction or metabolic acidosis are also typical signs of sepsis. Sepsis is caused by severe infection by bacteria, viruses, parasites or fungi. Moreover, there are cofounding factors which inferior influence the onset or outcome of sepsis such as diabetes or cancer. Preferably, sepsis is referred to in accordance with the present invention is characterized by the presence of two or more of the following symptoms in response to an infection: abnormal temperature (preferably, below 36° C. or above 38° C.), abnormal heart rate (preferably, above 90 beats/min), abnormal respiratory rate (preferably, above 20 breathings/min) or blood gas composition (preferably, $CO_2$ less than 4.3 kPa) and abnormal white blood cell number (preferably, less than $4 \times 10^9$/L or more than $12 \times 10^9$/L or histological presence of band neutrophils).

Advantageously, it has been found in the studies underlying the present invention that a fusion polypeptide comprising an Fc portion of an immunoglobulin and the extracellular portion of the human B7-H1 polypeptide can be used for efficiently treating and/or preventing organ failure in a subject suffering from sepsis. Specifically, it was found that the aforementioned fusion polypeptide or variants thereof are capable of binding to cytotoxic T cells, thereby inhibiting sepsis-induced T-cell cytotoxicity and preventing organ failure. Moreover, it was found that downregulation of the B7-H1 protein allows autoimmune CTL activation during sepsis. Maintaining B7-H1 expression or applying the fusion polypeptide of the invention significantly improves liver damage. Mechanistically, B7-H1 was downregulated by reactive oxygen species (ROS) formation. Thus, the fusion polypeptide according to the invention shall, preferably, upon administration inhibit sepsis-induced cytotoxic T-cells in the subject. Moreover, it shall, preferably, upon administration induce a long-lasting tolerance in cytotoxic T-cells in the subject against sepsis-caused activation. Consequently, it can be surprisingly applied in a therapeutic as well as preventive manner.

The above explanations and definitions of the terms apply throughout the specification. Moreover, in the following, typical embodiments of the fusion polypeptide for use according to the present invention are listed.

In a preferred embodiment of the fusion polypeptide for use according to the invention, said organ failure is CD8 cytotoxic T-cell dependent multi-organ failure.

In a further preferred embodiment of the fusion polypeptide for use according to the invention, said immunoglobulin is human IgG.

In yet a preferred embodiment of the fusion polypeptide for use according to the present invention, said extracellular portion of the human B7-H1 polypeptide or variant thereof is selected from the group consisting of:
(a) a polypeptide having an amino acid sequence encoded by the nucleic acid sequence shown in SEQ ID NO: 1 or 5;
(b) a polypeptide having an amino acid sequence shown in SEQ ID NO: 2 or 6;
(c) a polypeptide remaining capable of binding to the PD1 polypeptide and having an amino acid sequence which is at least 70% identical to the amino acid sequence of the polypeptide of (a) or (b), and
(d) a polypeptide remaining capable of binding to the PD1 polypeptide having an amino acid sequence according to (a) or (b) which comprise at least one of the following amino acid exchanges L27A, S34Y, D49S, Y56S, E58S, K62S, H69F, E72S, K75S, K89S, A98F, Q100S, R113Y, and S117Y.

In a further preferred embodiment of the fusion polypeptide for use according to the present invention, said fusion polypeptide comprises (iii) a third portion being a polypeptide capable of binding specifically to cytotoxic T-cells.

More preferably, said polypeptide capable of binding specifically to cytotoxic T-cells is selected from the group consisting of: a polypeptide comprising a portion of the MHC-I complex which is capable of binding to CD8, a portion of the CD80 which is capable of binding to CD28, a polypeptide being an antibody or fragment thereof capable of specifically binding to CD8, a polypeptide being an antibody or fragment thereof capable of specifically binding to CD28, and CD2-binding portion of lymphocyte function associated antigen-3 (LFA-3).

In a preferred embodiment of the fusion polypeptide for use according to the invention, said at least the first portion and at least the second portion are permanently or reversible linked to each other.

In yet a preferred embodiment of the fusion polypeptide for use according to the invention, said subject is a mammal, preferably a human.

In a further preferred embodiment of the fusion polypeptide for use according to the invention, said fusion polypeptide is to be applied once as a bolus or is to be applied at least twice.

In a preferred embodiment of the fusion polypeptide for use according to the invention said fusion polypeptide is to be applied together with at least one further drug.

More preferably, said at least one further drug is selected from the group consisting of: antibiotics, vasopressors, steroids, anticoagulants, antithrombotics, proinflammatory cytokines and DAMP inhibitors.

In a preferred embodiment of the fusion polypeptide for use according the present invention, said fusion polypeptide upon administration inhibits sepsis-induced cytotoxic T-cells in the subject.

In another preferred embodiment of the fusion polypeptide for use according to the invention, said fusion polypeptide upon administration induces a long-lasting tolerance in cytotoxic T-cells in the subject against sepsis-caused activation.

The present invention, furthermore, relates to a polynucleotide for use in treating and/or preventing organ failure in a subject suffering from sepsis, said polynucleotide encoding a fusion polypeptide defined in accordance with the present invention.

The term "polynucleotide" as used herein refers to single- or double-stranded DNA molecules as well as to RNA molecules. Encompassed by the said term is genomic DNA, cDNA, hnRNA, mRNA as well as all naturally occurring or artificially modified derivatives of such molecular species. The polynucleotide may be, preferably, a linear or circular molecule. Moreover, in addition to the nucleic acid sequences encoding the aforementioned fusion polypeptide, a polynucleotide according to the present invention may comprise additional sequences required for proper transcription and/or translation such as 5'- or 3'-UTR sequences or sequences required for splicing or RNA stability. Preferred polynucleotides encoding the fusion polypeptide according to the present invention are also described above in more detail.

In a preferred embodiment of the polynucleotide for use according to the present invention, said polynucleotide is comprised in an expression construct allowing for expression of the said polynucleotide in the said subject.

The term "expression construct" as used herein refers to a heterologous polynucleotide comprising the aforementioned polynucleotide encoding the fusion polypeptide as well as nucleic acids being heterologous thereto which are required for expression of the polynucleotide encoding the fusion polypeptide. Typically, such heterologous nucleic acids may be promoter sequences, enhancer sequence and/or transcription termination sequences such as terminators. Moreover, the expression construct may also comprise further nucleic acids required for introducing the expression construct into a host. For example, if expression in host cells is desired, the expression construct may comprise further nucleic acids required for transformation or transfection and for propagation of the introduced expression construct in the host cells.

Preferably, the expression construct referred to herein may be a vector. A vector as meant herein, preferably, encompasses phage, plasmid, viral or retroviral vectors as well as artificial chromosomes, such as bacterial or yeast artificial chromosomes. The vector encompassing the polynucleotide encoding the fusion polypeptide, preferably, further comprises selectable markers for propagation and/or selection in a host. The vector may be incorporated into a host cell by various techniques well known in the art. For example, a plasmid vector can be introduced in a precipitate such as a calcium phosphate precipitate or rubidium chloride precipitate, or in a complex with a charged lipid or in carbon-based clusters, such as fullerens. Alternatively, a plasmid vector may be introduced by heat shock or electroporation techniques. Should the vector be a virus, it may be packaged in vitro using an appropriate packaging cell line prior to application to host cells. Retroviral vectors may be replication competent or replication defective. In the latter case, viral propagation generally will occur only in complementing host/cells. Moreover, the polynucleotide is usually operatively linked to expression control sequences allowing expression in prokaryotic or eukaryotic host cells or isolated fractions thereof in the said vector. Expression of the polynucleotide comprises transcription of the polynucleotide into a translatable mRNA. Regulatory elements ensuring expression in host cells are well known in the art. Preferably, they comprise regulatory sequences ensuring initiation of transcription and/or poly-A signals ensuring termination of transcription and stabilization of the transcript. Additional regulatory elements may include transcriptional as well as translational enhancers. Possible regulatory elements permitting expression in prokaryotic host cells comprise, e.g., the lac-, trp- or tac-promoter in E. coli, and examples for regulatory elements permitting expression in eukaryotic host cells are the AOX1- or the GAL1-promoter in yeast or the CMV-, SV40-, RSV-promoter (Rous sarcoma virus), CMV-enhancer, SV40-enhancer or a globin intron in mammalian and other animal cells. Other expression systems envisaged by the invention shall permit expression in insect cells, such as polyhedrin promoter based systems. Moreover, inducible expression control sequences may be used in an vector encompassed by the present invention. Such inducible vectors may comprise tet or lac operator sequences or sequences inducible by heat shock or other environmental factors. Suitable expression control sequences are well known in the art. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pBluescript (Stratagene), pCDM8, pRc/CMV, pcDNA1, pcDNA3 (Invitrogen) or pSPORT1 (Invitrogen) or baculovirus-derived vectors. Preferably, said vector is an expression vector and a gene transfer or targeting vector. Expression vectors derived from viruses such as retroviruses, vaccinia virus, adeno-associated virus, herpes viruses, or bovine papilloma virus, may be used for delivery of the expression constructs according to the invention into targeted cell population, e.g. also in gene therapeutic approaches. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994).

Further, it might be envisaged to introduce the expression construct into the genome of a host. In such a case, the expression construct may also comprise nucleic acids that allow for either heterologous or homologous integration of the said expression construct. Thus the expression construct referred to herein may also be a targeting constructs which allow for random or site-directed integration of the targeting construct into genomic DNA. Such target constructs, preferably, comprise DNA of sufficient length for either homologous or heterologous recombination flanking the expression cassette with the polynucleotide encoding the fusion polypeptide. Moreover, the expression construct may also be introduced using integration systems like Cre/LoxP or CRISPR/CAS. In such cases, the expression construct may comprise further nucleic acids allowing for the use of such integration systems. Suitable modifications/additions depend on the envisaged integration system and are well known for those skilled in the art.

It will be understood that the present invention furthermore provides for the use of the above defined fusion polypeptide or polynucleotide for the manufacture of a medicament for treating and/or preventing organ failure in a subject. Typically, the fusion polypeptide or polynucleotide as well as the subjects to be treated or the diseases referred to have the preferred characteristics defined above.

It will be understood that the present invention also provides for a method of treating and/or preventing organ failure in a subject.

In particular, provided is a method of treating organ failure in a subject suffering from sepsis, said method comprising (a) administering to said subject a therapeutically effective amount of a fusion polypeptide comprises at least (i) a first portion being an Fc portion of an immunoglobulin and (ii) a second portion comprising the extracellular portion of the human B7-H1 polypeptide or a variant thereof or (b) administering a therapeutically effective amount of a polynucleotide encoding said fusion polypeptide.

Typical aspects of the invention with respect to the kind of organ failure, the subjects to be treated, sepsis, and the fusion polypeptide or the polynucleotide are described above and apply mutatis mutandis for the present method of treating and/or preventing organ failure in a subject.

In yet another typical aspect of the aforementioned method of the invention, said method may encompass identification of a subject to be treated by determining the presence of sepsis prior to administering the fusion polypeptide or polynucleotide encoding it.

In another typical aspect of the aforementioned method of the invention, said method comprises monitoring the subjects for signs of organ failure after administration of the fusion polypeptide and, if necessary, administering the fusion polypeptide or polynucleotide encoding it again or at a difference dosage.

All references cited in this specification are herewith incorporated by reference with respect to their entire disclosure content and the disclosure content specifically mentioned in this specification. Full citations of the references are to be found elsewhere herein.

FIGURES

FIG. 1: Enhanced number of CD8+ T cells in livers of septic mice. 24 h following sham- or CLP-operation, mice were sacrificed. Livers were removed to prepare single cell suspensions. Cell subpopulations were determined by FACS analysis. A quantification of five mice of each treatment is provided.

Figure 2:
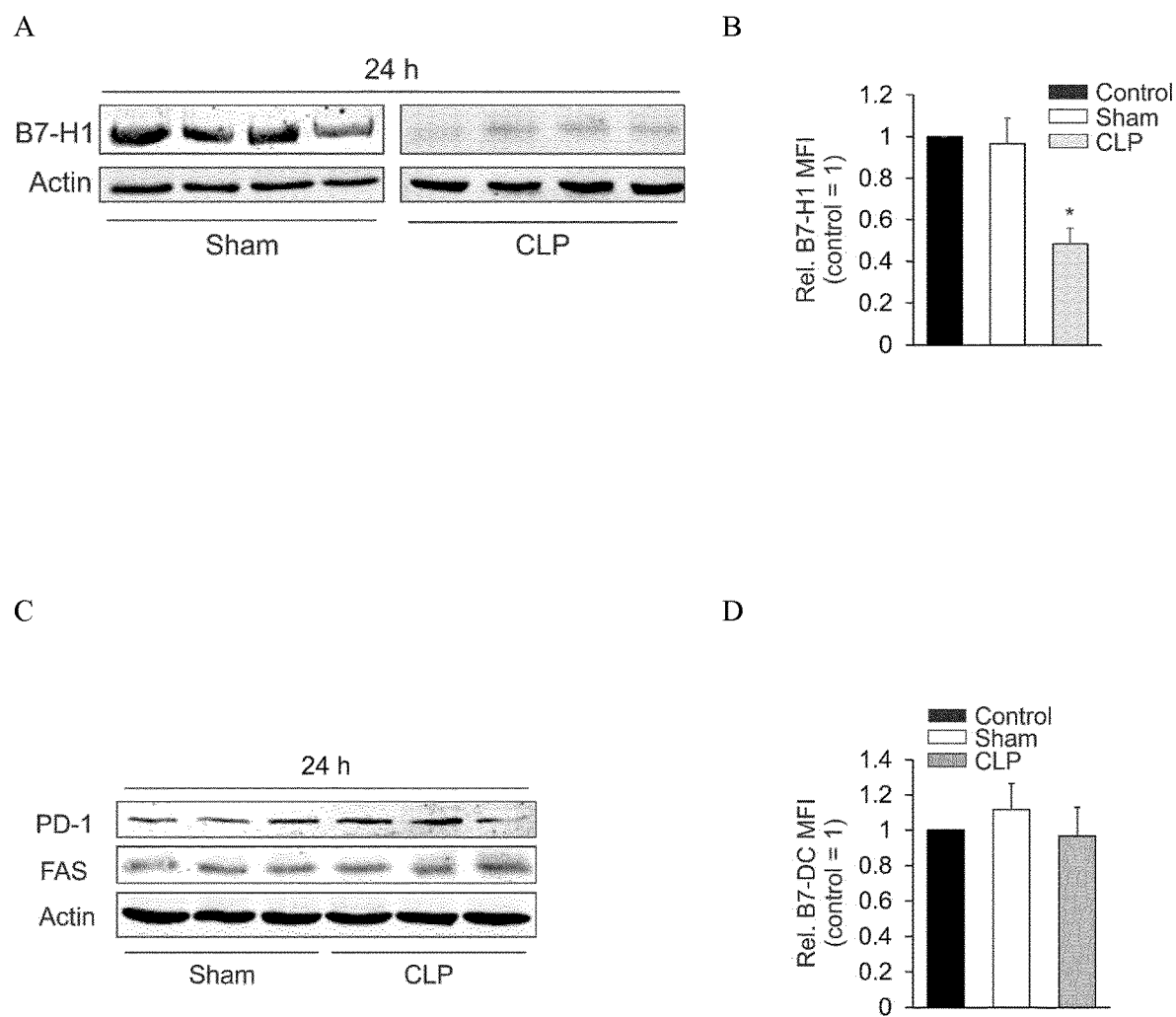

FIG. 2: Expression of B7-H1, B7-DC, Fas and PD-1 in the liver following CLP. 24 h following sham- or CLP-operation, mice were sacrificed. Livers were removed to prepare single cell suspensions. Total lysates were prepared in (A) and (C) to analyze expression of B7-H1, PD-1, and Fas. Hepatocyte specific expression of (B) B7-H and (D) B7-DC surface expression was performed by FACS analysis. All experiments were performed at least five times. Data represent the mean±SD (*$p<0.5$) or show representative blots.

Figure 3:
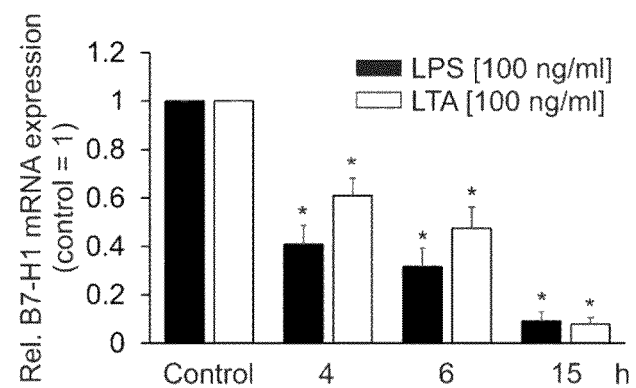
Figure 3:
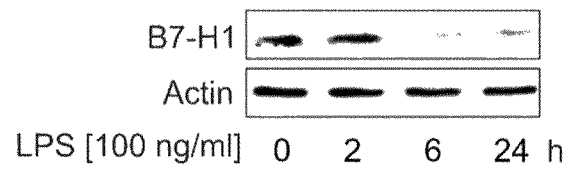

FIG. 3: B7-H1 expression in Hepa1-6 cells following LPS or LTA stimulation. Hepa1-6 cells were stimulated for the indicated times with 100 ng/ml LPS or 100 ng/ml LTA. Afterwards cells were harvested and mRNA was isolated or protein lysates were prepared as described in Materials and Methods. mRNA expression of B7-H1 (A) was analyzed by quantitative PCR. 18s rRNA was used as a house keeping gene. (B) B7-H1 protein expression following LPS stimulation was determined by Western analysis. All experiments were performed at least five times. Data represent the mean±SD (*p<0.5) or show a representative blot.

Figure 4:
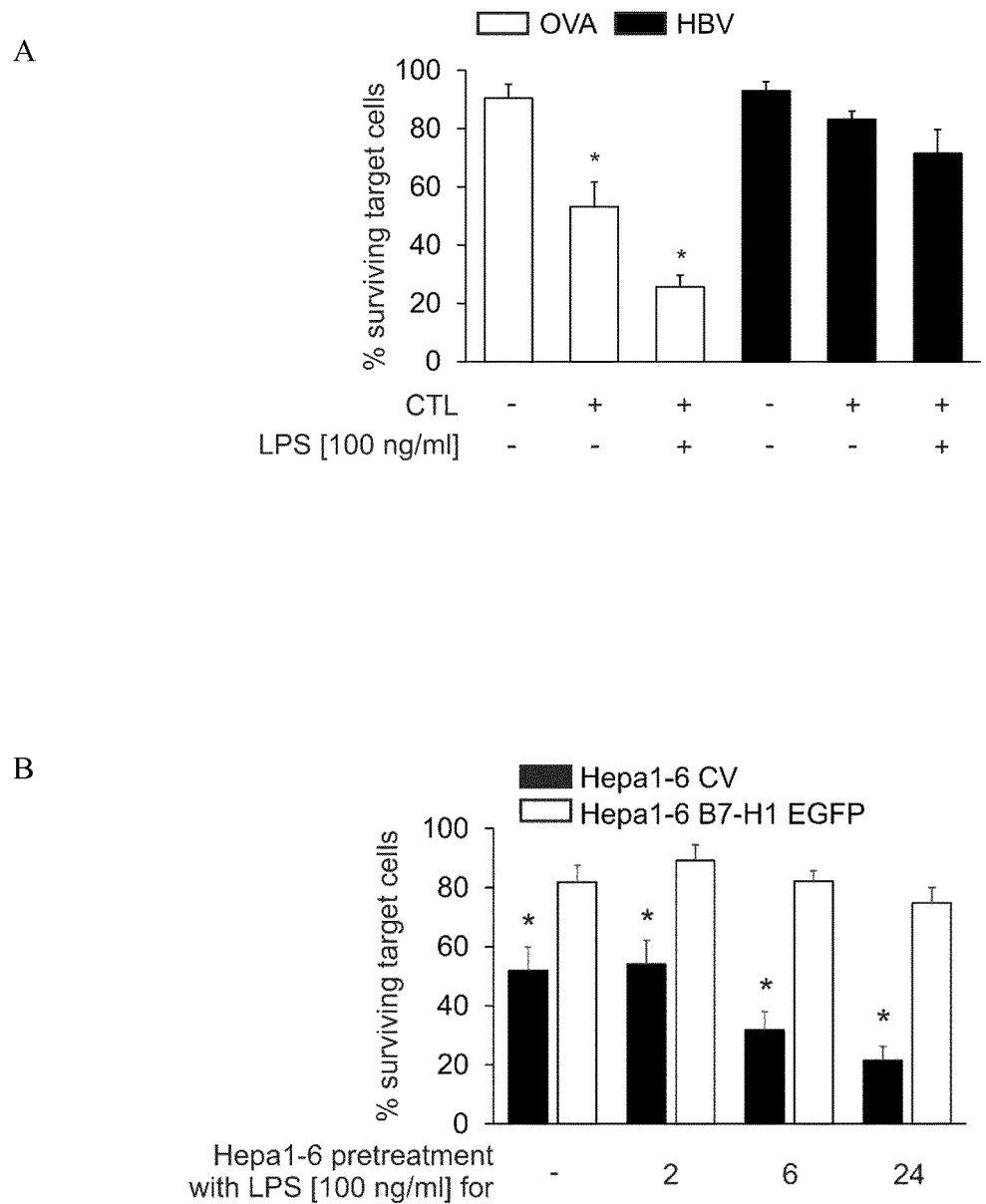

FIG. 4: LPS-dependent B7-H1 downregulation enhances CTL-mediated cytotoxicity. Cytotoxic T cells were isolated and enriched from spleen of OT-I mice as described under Materials and Methods as effector cells. Hepa1-6 cells were used as target cells. (A) To establish the cytotoxicity assay Hepa1-6 cells were pulsed for 2 h with XY µg/ml of the ovalbumin peptide 257-264 (OVA) or the hepatitis B virus (HBV) control peptide. Hepa1-6 cells were treated for 24 h with LPS [100 ng/ml] or remained untreated as controls. Afterwards, Hepa1-6 cells were stained with CellTracker-Orange™ and incubated for 24 h with cytotoxic T cells (target vs. effector cell ratio 1:5). The number of surviving target cells was determined by FACS analysis. A quantification of five independent experiments is provided. Data represent the mean±SD (*p<0.5). (B) Hepa1-6 cells were stably transduced with a vector encoding B7-H1 EGFP or a control vector (CV). Following FACS enrichment, positive cells were stimulated for the indicated times with LPS [100 ng/ml] or remained untreated as control. Afterwards, Hepa1-6 cells were stained with CellTrackerOrange™ and incubated for 24 h with cytotoxic T cells (target vs. effector cell ratio 1:5). The number of surviving target cells was determined by FACS analysis. A quantification of five independent experiments is provided. Data represent the mean±SD (*p<0.5).

Figure 5:
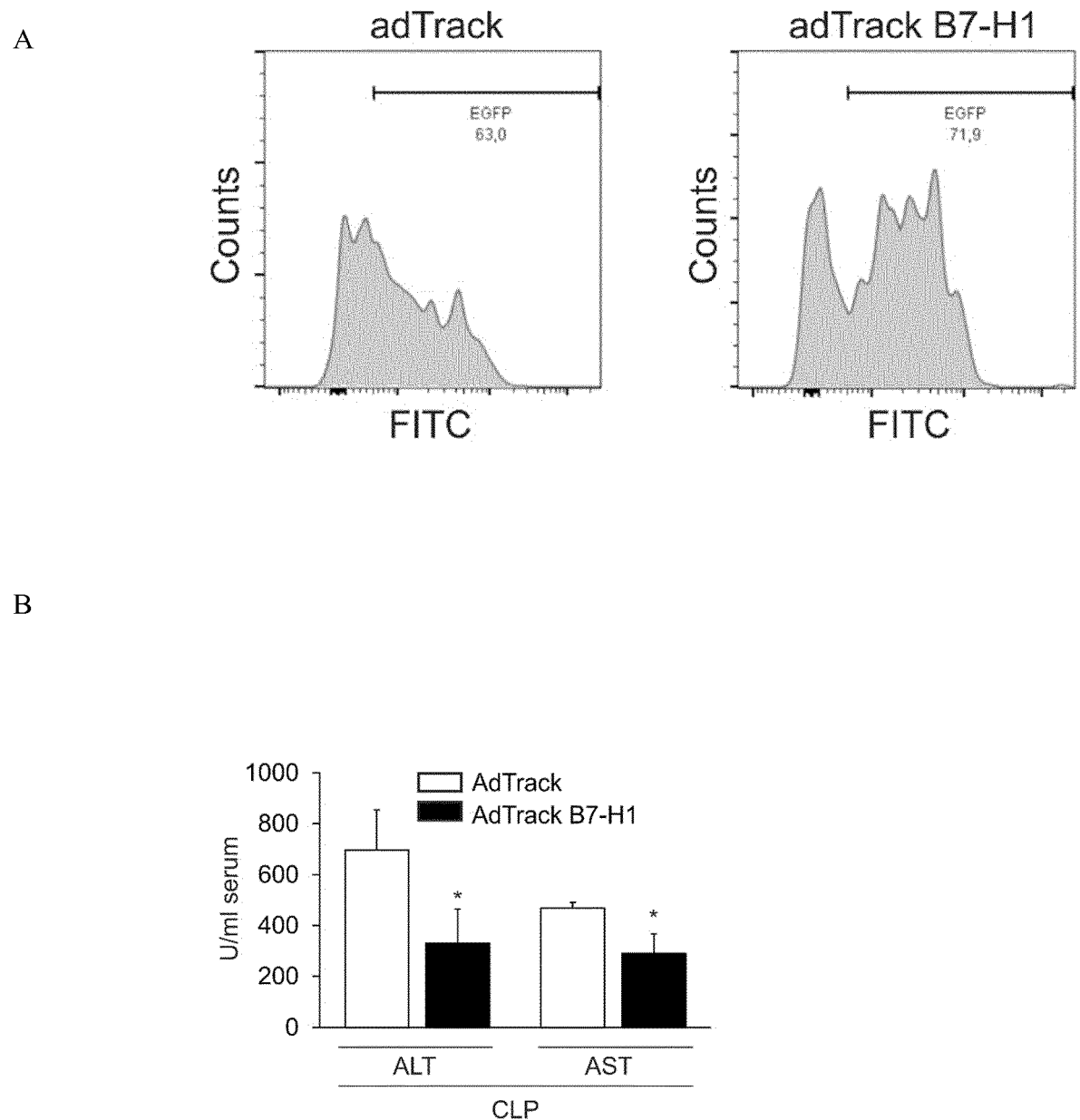

FIG. 5: Adenoviral B7-H1 expression ameliorates liver damage following CLP. Mice were injected intravenously 5×10⁹ adenoviral particles encoding EGFP (adTrack) or B7-H1 EGFP (adTrack B7-H1). 4 days following administration of adenoviral particles mice were subjected to polymicrobial sepsis by CLP operation. After 24 h mice were sacrificed, livers were removed and blood was collected. Transduction efficiency was determined by FACS analysis in liver single cell suspensions, gated for non-immune cells, i.e. CD45—(A). One representative result is shown. Serum was isolated from blood and ALT/AST release determined with a Reflotron Plus hematology analyzer (B). Results of 4 mice each are shown.

Figure 6:
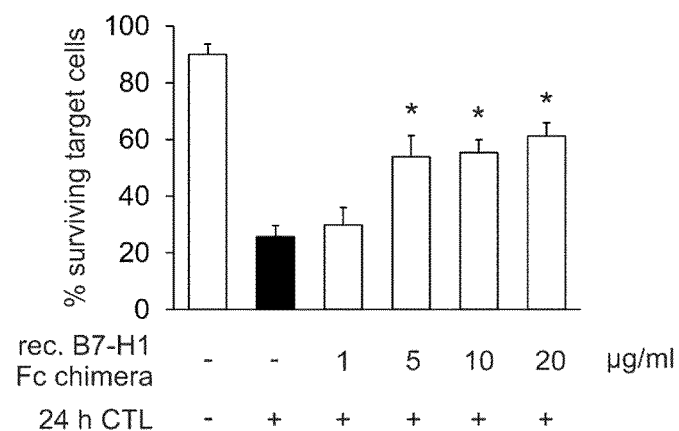
Figure 6:
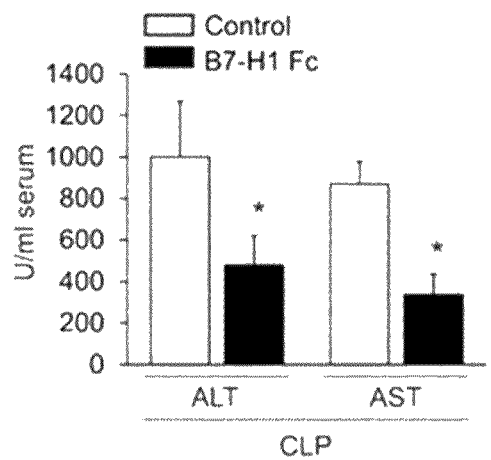

FIG. 6. Recombinant B7-H1 Fc chimera prevents liver damage during sepsis. (A) Cytotoxic T cell-dependent hepatocyte killing was determined using Hepa1-6 cells as target cells and CD8+ T cells derived from OT-I mice as effector cells. CellTrackerOrange™ stained Hepa1-6 cells were pulsed for 2 h with the OVA257-264 peptide. Afterwards, Hepa1-6 cells were co-cultured with enriched CD8+ T cells derived from the spleen of OT-I mice in a ratio of 5:1 (effector: target cells). In parallel, recombinant B7-H1 Fc was added in the indicated concentrations. The number of surviving target cells was examined by FACS analysis. A quantification of five independent experiments is provided. Data represent the mean±SD (*p<0.5). (B) Wild type mice were subjected to CLP-operation. Directly afterwards, B7-H1 Fc was applied intravenously. PBS alone was administered as a solvent control. Liver damage in following CLP operation is assessed by determining the ALT/AST release into the serum, which is examined with a Reflotron Plus hematology analyzer (B7-H1 Fc treated vs. control; CLP; n=5/5, *p<0.5).

Figure 7:
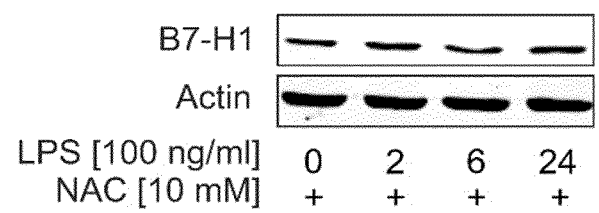

FIG. 7: B7-H1 expression was restored adding the GSH precursor N-acetyl-cysteine (NAC). Hepa1-6 cells were stimulated for the indicated times with 100 ng/ml LPS with 10 mM NAC. Afterwards cells were harvested and protein lysates were prepared as described in Materials and Methods. B7-H1 protein expression was determined by Western analysis. All experiments were performed at least five times. A representative blot is shown.

Figure 8:
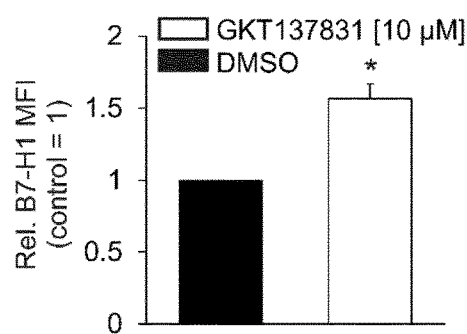
Figure 8:
Figure 8:
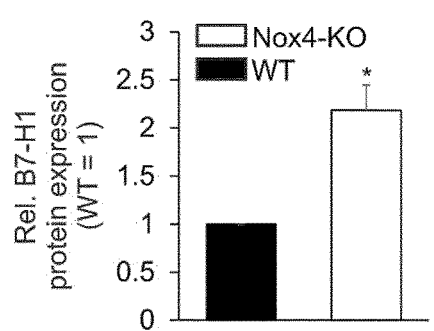
Figure 8:
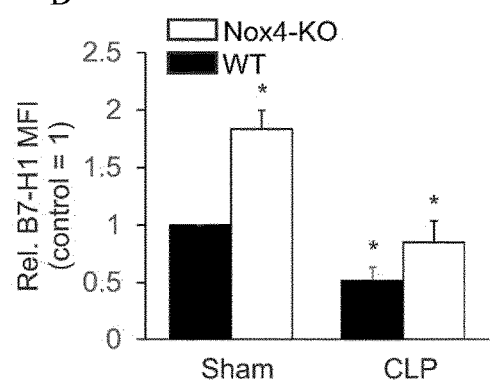
Figure 8:
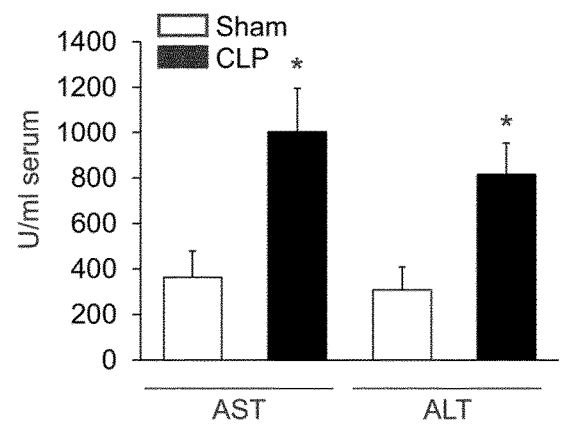

FIG. 8: Inhibition of Nox4 enhances B7-H1 expression. Hepa1-6 cells were treated with the Nox4-specific inhibitor GKT137831 [10 µM] for 24 h. Afterwards, cells were harvested and B7-H1 expression was determined by FACS analysis. A quantification of five independent experiments is provided in (A). In liver homogenates of global NOX4 knockout mice B7-H1 protein expression was examined by Western blotting (B). A representative blot is shown. A quantification of B7-H1 expression (WT vs. NOX4-KO; n=5/5; *p<0.5) is provided in (C). B7-H1 expression on hepatocytes following polymicrobial sepsis initiation by cecal ligation and puncture (CLP) was studied in liver single cell suspensions by FACS-analysis gating for CD45-, i.e. non-immune cells as described in Materials and Methods. A quantification is shown (D), (sham vs. CLP, WT sham is set as 1; n=5/5/5/5; *p<0.5). Liver damage in global NOX4 knockout mice following CLP operation is assessed by looking at ALT/AST release into the serum, which is determined with a Reflotron Plus hematology analyzer (E) (NOX4-KO; sham vs. CLP; n=5/5, *p<0.5).

Figure 9:
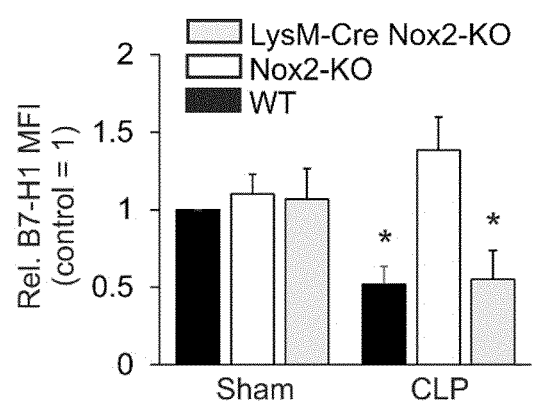
Figure 9:
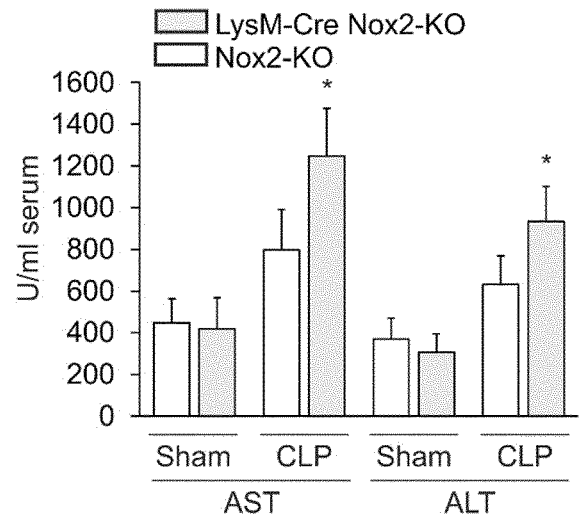

FIG. 9: Global NOX2-knockout restores hepatic B7-H1 expression during sepsis. Mice with a global NOX2 knockout (NOX2-KO) and with myeloid lineage-specific knockout (LysM-Cre NOX2-KO) as well as wild type littermates (WT) were used. 24 h following CLP- or sham-operation, mice were sacrificed. Blood was collected and liver was removed. (A) B7-H1 protein expression on hepatocytes was determined in liver single cell suspensions by FACS-analysis gating for CD45-, i.e. non-immune cells as described in Materials and Methods. (WT vs. NOX2-KO vs. LysM-Cre NOX2-KO; sham vs. CLP; sham treated WT is set as 1; n=5/5/5; *p<0.5). (B) Serum was isolated from blood and ALT/AST release was determined with a Reflotron Plus hematology analyzer. (LysM-Cre NOX2-KO vs. NOX2-KO; sham vs. CLP; n=5/5/5/5; *p>0.5).

Figure 10:
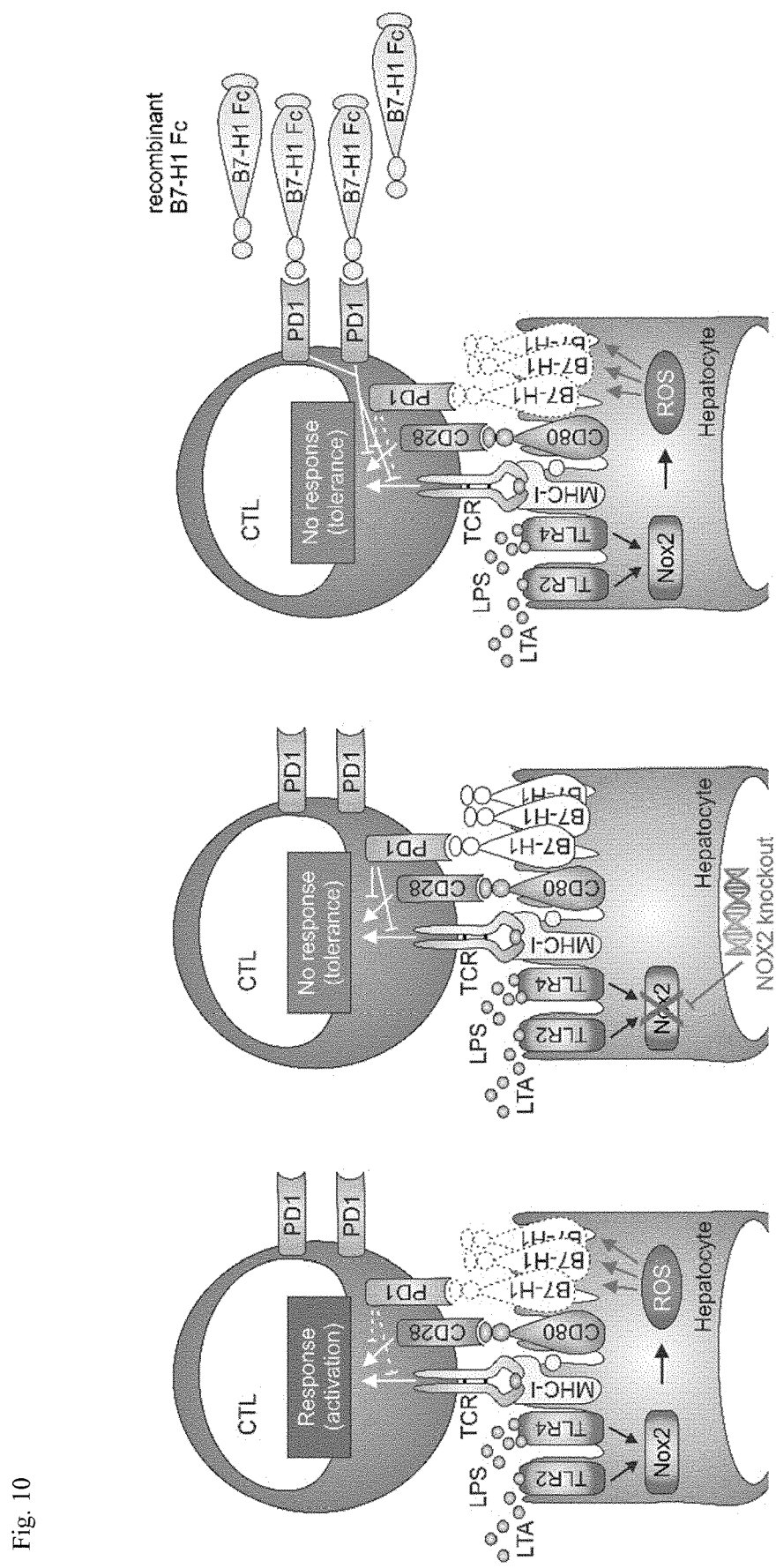

FIG. 10: Maintaining B7-H1 expression during sepsis—a new therapeutic approach. (A) During polymicrobial sepsis, reactive oxygen species (ROS) are formed most likely by hepatic Nox2 in response to bacterial components, such as LPS or LTA. These ROS downregulate expression of the co-inhibitory protein B7-H1 on the surface of hepatocytes, which consequently allows activation of cytotoxic T cells (CTL) in an autoimmune fashion. Maintaining B7-H1 expression by genetic deletion of the ROS-generating enzyme Nox2 (B) or exogenously administering recombinant B7-H1 (C) keeps CTL tolerant, thus improving septic outcome.

EXAMPLES

The invention will be merely illustrated by the following Examples. The said Examples shall, whatsoever, not be construed in a manner limiting the scope of the invention.

Example 1: Cytotoxic T Cells (CTLs) Accumulate in the Liver of Septic Mice

During sepsis, organ failure, often followed by a multi-organ-dysfunction syndrome (MODS), frequently results in the patient's death. Therefore, understanding mechanisms leading to organ damage are mandatory to improve already existing care options or to set up new therapy approaches. Von Knethen et al., 2015 demonstrated that CTLs are activated in an autoimmune fashion in a murine sepsis model while activation of CD8+ T cells has been shown to be involved in liver damage in this sepsis mouse model (Wesche Soldato et al., 2007a). To characterize the underlying principle, the number of CTLs in livers derived from sham-vs. cecalligation and puncture-(CLP)-operated mice was analyzed. As shown in FIG. 1, an increased CTL count in livers derived from septic mice 24 h following CLP operation compared to sham treated or control mice, respectively, could be found. This result suggests an activation induced migration of CTL into the liver tissue.

Example 2: Expression of B7-H1 is Downregulated in a Polymicrobial Sepsis Model

Autoimmune CTL activation is typically prevented by co-inhibitory proteins such as B7-H1, also named CD274 or PD-L1, or B7-DC designated CD273 or PD-L2 as well (Butte et al., 2007; Sharpe et al., 2007). These co-inhibitory proteins are typically expressed on antigen presenting cells (APC), which are most likely hepatocytes in the case of the polymicrobial sepsis model (Ueki et al., 2011). Thus, expression of these co-inhibitory factors was analyzed in the liver following CLP. Expression of B7-H1 was downregulated on total protein level (FIG. 2A) and on the cell surface (FIG. 2B). In contrast, mRNA and protein expression of its re-ceptor PD-1 was not altered (FIG. 2C). Expression of Fas (also known as CD95, the receptor for Fas ligand) known to play an important role in the regulation of the immune response in mice and humans (Galle et al., 1995; Hanabuchi et al., 1994) was also unaltered (FIG. 2C). The total protein expression of B7-DC was very low (data not shown) and its cell surface expression was not changed 24 h following CLP operation (FIG. 2D).

Example 3: Cell Wall Components of Gram-Positive and Gram-Negative Bacteria Downregulate B7-H1 Expression in Hepa1-6 Cells Primary cultures of hepatocytes express mRNA for all TLRs and respond to TLR2 and TLR4 ligands (Seki and Brenner, 2008). Therefore, bacterial components, which are available in the liver during sepsis, may account for a decrease in B7-H1 expression in hepatocytes. To elucidate the mechanism provoking this downregulation, a cell culture model based on the murine hepatoma cell line Hepa1-6 (Darlington, 1987) was established. This cell line has been shown to express TLR2 and -4 (Matsumura et al., 2000; Romics et al., 2004). To mimic bacterial infection, Hepa1-6 cells were treated with LPS, a cell wall component of gram-negative bacteria and LTA, a cell wall constituent of gram-positive bacteria. As depicted in FIG. 3, B7-H1 expression was decreased in response to stimulation with both of the two bacterial components on mRNA (FIG. 3A) and protein (FIG. 3B) level in a time-dependent manner. However, it still remains elusive whether LPS- or LTA-stimulation make hepatocytes more susceptible to CTL-dependent cytotoxicity and whether maintaining B7-H1 expression protects towards autoimmune CTL activation.

Example 4: LPS-Treated Hepa1-6 Cells are More Susceptible to CTL-Dependent Cytotoxicity To clarify whether LPS- or LTA-stimulation make hepatocytes more susceptible to CTL-dependent cytotoxicity or whether maintaining B7-H1 expression protects towards autoimmune CTL activation, a syngeneic cytotoxicity assay with CTLs derived from OT-1 mice (haplotype H2Kb) as effector cells (Clarke et al., 2000) and Hepa1-6 cells, derived originally from C57L mice (haplotype H2Kb) as target cells was set up. Hepa1-6 cells were treated for 24 h with LPS or remained as control. Afterwards, cells were pulsed for 2 h with the ovalbumin peptide 257-264 (OVA257-264) or the hepatitis B-virus (HBV)-derived peptide ILSPFLPLL derived from the HBV surface antigen (HBsAg) as control. Cells were washed twice in PBS, stained with CellTracker-Orange™, and incubated in a ratio of 1:5 (target vs. effector cells) with CTLs for 24 h. Surviving cells were determined by FACS analysis. In the control situation, i.e. untreated Hepa1-6 cells incubated with CTLs, roughly 50% of the target cells were killed (FIG. 4A). Following LPS-stimulation of Hepa 1-6 cells, cytotoxicity was enhanced to approximately 70% dead target cells when Hepa1-6 cells were pulsed with the OVA257-264 peptide. In contrast, HBV peptide pulsed Hepa 1-6 cells were killed significantly less by CTLs.

Example 5: Overexpression of B7-H1 Protects Hepa1-6 Cells Towards CTL-Dependent Cytotoxicity To verify that maintaining B7-H1 expression blocks CTL-dependent cytotoxicity in vitro, Hepa1-6 cells were stably transduced with a lentiviral vector encoding for B7-H1 linked to EGFP. Following FACS sorting, these B7-H1 overexpressing cells as well as control virus transduced cells were used in the cytotoxicity assay (FIG. 4B). As expected, B7-H1 overexpressing cells were protected towards CTL-dependent killing (FIG. 4B, white columns), whereas cytotoxicity towards control virus transduced cells was roughly 50% without LPS stimulation and was enhanced following LPS (100 ng/ml] treatment in a time-dependent manner (FIG. 4B, black columns).

Example 6: Maintaining B7-H1 Expression Inhibits Liver Damage after CLP

To investigate a pathophysiological role in the polymicrobial sepsis mouse model in vivo, an adenoviral approach to overexpress B7-H1 in the liver was established. FIG. 5A shows that a hepatocyte transduction efficiency of around 70% could be achieved. Mice were kept for four days untreated to recover from the adenoviral transduction, which consequently induces an anti-viral immune response of the mice. After that time, CLP was initiated for 24 h. Then, mice were sacrificed and serum was isolated from mice blood to determine disease severity by analyzing the liver damage markers ALT and AST. As shown in FIG. 5B, overexpression of B7-H1 improved liver damage, i.e. significantly reduced ALT/AST levels. Maintaining B7-H1 expression as a therapeutic approach can be achieved by exogenously adding B7-H1. In an in vitro cytotoxicity assay with OVA257-264 pulsed Hepa1-6 as target cells and OT-I mice derived CTLs as effector cells, simultaneous addition of recombinant B7-H1 Fc chimera inhibited CTL-mediated cytotoxicity (FIG. 6A). While 1 µg/ml recombinant B7-H1 Fc chimera did not alter killing of target cells, 5 µg/ml enhanced target cell survival up to approximately 50%. Increasing recombinant B7-H1 Fc chimera concentration up to 20 µg/ml does not enhance target cell survival. To translate the in vitro result to the in vivo situation, recombinant B7-H1 Fc chimera was applied intravenously (i.v.) into the tail vein, directly after the CLP operation. Twenty-four hours afterwards, blood of mice was collected and serum was prepared. The release of liver damage markers ALT/AST was determined. As shown in FIG. 6B, the application of recombinant B7-H1 Fc chimera significantly reduced ALT/AST release, which is indicative of an improvement in septic outcome in vivo.

Example 7: ROS-Dependent Downregulation of B7-H1

LPS and LTA act via different Toll-like receptors (TLRs) on target cells i.e. TLR2 for LTA and TLR4 for LPS. Binding to these receptors has been shown to trigger various signaling cascades, i.e. NADPH oxidase-mediated redox signaling. The NADPH oxidase NOX4 has been shown to constitutively generate reactive oxygen species (ROS) such as O2- or H2O2 (Dikalov et al., 2008). Recent data support the assumption that O2- is not only generated to kill pathogens but acts as second messenger as well (Brune et al., 2013). To investigate whether a ROS-dependent mechanism was responsible for the reduction of B7-H1, ROS formation was determined in Hepa 1-6 cells treated with LPS alone or in combination with N-acetylcysteine (NAC). Treatment with the ROS inhibitor NAC restored expression of B7-H1 (see FIG. 7 vs. FIG. 3B).

Example 8: Inhibition of Nox4 Enhances B7-H1 Expression

The NADPH oxidase 4 (Nox4) has been shown to be expressed in Hepa1-6 cells (Boudreau et al., 2009) and to provoke a constitutive production of H2O2, which—upon stimulation—may be enhanced. To evaluate whether Nox4 plays a role in the regulation of B7-H1 expression, Hepa1-6 cells were incubated with the specific Nox4 inhibitor GKT137S31 [10 µM] for 24 h without any further treatment (Jiang et al., 2012). As shown in FIG. 8A, Nox4 inhibition increased B7-H1 surface expression up to roughly 50% in Hepa1-6 cells. Furthermore, livers from global NOX4-knockout mice were isolated and a total lysate Western analysis was performed. FIG. 8B shows that B7-H1 is upregulated in livers derived from Nox4-deficient mice compared to wild type controls. A densitometric quantification provided in FIG. 8C demonstrated a roughly two-fold higher expression of B7-H1 in NOX4-knockout mice derived livers. An analysis of B7-H1 surface expression in hepatocytes showed a similar rise in B7-H1 expression (FIG. 8D, left columns). Using these mice with the CLP model, a downregulation of B7-H1 expression could be observed in both, the wild type as well as the knockout mice (FIG. 8D, right columns). However, expression of B7-H1 in Nox4-deficient cells still remained a little higher compared to wild type mice 24 h following sepsis initiation by CLP. Despite this, disease severity was not improved in NOX4-knockout mice (FIG. 8E). Therefore, blocking Nox4 activity can be excluded as a means to improve sepsis survival.

Example 9: Global NOX2 Deletion Prevents B7-H1 Downregulation During Polymicrobial Sepsis The experimental sepsis model was next evaluated using global NOX2-deficient (NOX2-KO) as well as mice with a NOX2-knockout specific for the myeloid lineage (LysM-Cre Nox2-KO). As shown in FIG. 9A, expression of B7-H1 in hepatocytes was similar 24 h following sham operation in all three genotypes. Interestingly, 24 h after CLP, expression of B7-H1 was downregulated in wild type (black column) and mice with a Nox-2 deletion in the myeloid lineage (grey column), whereas in mice with a global NOX2-knockout (white column) B7-H1 expression remained high. The release of liver damage markers into the serum revealed a significant increase in ALT and AST in mice with a myeloid lineage NOX2-deletion (FIG. 9B, grey columns), but remained weak in global NOX2-knockout mice (FIG. 9B, white columns).

Example 10: General Methods and Material

Mice with a specific NOX2 knockout for the myeloid lineage were generated by crossing C57Bl/6 mice bearing conditional loxP-flanked alleles of NOX2 (NOX2fl/fl), kindly provided by Prof. Shah (King's College London BHF Centre of Excellence, London, UK) with C57Bl/6N-(Tg) LysM-Cre transgenic mice, where the Cre recombinase has been knocked in behind the LysM promoter (Akiyama et al., 2002; Cui et al., 2002; Hennet et al., 1995; Hume, 2011; Schmidt et al., 2011). Global NOX2- and NOX4 knockout mice as well as wild type mice were used on a C57Bl/6 background as well. Mice were kept in a temperature-controlled room with 12 h light and 12 h dark diurnal cycle. They were housed in filter-topped cages and were fed standard laboratory chow and water ad libitum. Genotypes were determined by PCR of tail DNA and deletion of NOX2 and NOX4 was confirmed by mRNA analysis (data not shown). All animal experiments followed the guidelines of the Hessian animal care and use committee (authorization no. F144/15).

The cecal ligation and puncture model (CLP) was performed as described previously (Rittirsch et al., 2009) or without ligation and puncture for sham mice (sham). Briefly, mice were anesthetized with ketamine (Ketavet®)/xylazine (Rompun®) 100 mg/200 mg per kg body weight. A midline laparotomy incision was performed in an aseptic fashion and one third of the cecum was ligated distal to the ileocecal valve, taking care not to disrupt bowel continuity. The ligated part was punctured through and through with a 20-gauge needle. Animals received i.p. 1 ml 0.9% NaCl immediately after surgery and buprenorphine (Temgesic®) 0.5 mg/kg after surgery s. c. and in the following time every 6 h. 24 h after CLP surgery, mice were sacrificed, spleens were dissected and a single cell suspension was prepared. CD8+ T cells were enriched to >95% by positive selection from spleens using the Dynabeads FlowComp Mouse CD8 Kit (Life Sciences, Heidelberg, Germany) following the distributors instructions. Purification was verified by FACS analysis using an anti-CD8α-FITC-labeled antibody (Euro-BioScience, Friesoythe, Germany). In some experiments, blood was taken before by heart puncture to isolate serum for determination of the two liver damage markers alanine- and aspartate aminotransferase. The amounts of the two enzymes were analyzed using a Reflotron Plus hematology analyzer (Roche Diagnostics, Mannheim, Germany) with the corresponding test strips. When liver was removed as well, the organ was flushed with PBS before. Afterwards, the liver was dissected and a single cell suspension prepared. Following CellTracker™ Orange (Life Technologies GmbH, Frankfurt, Germany) staining, these cells were directly used for the co-culture cytotoxicity assay with enriched CTL.

Hepa1-6 cells (Darlington, 1987) were cultured in RPMI1640 (PAA Laboratories) supplemented with 100 U/ml penicillin (PAA Laboratories), 100 µg/ml streptomycin (PAA Laboratories), and 10% heat inactivated fetal calf serum (PAA Laboratories).

To overexpress murine B7-H1 in vitro, we amplified B7-H1 from murine mRNA of Hepa1-6 cells by PCR using the following primer pair (NM_021893): forward 5'-CGC CCG GGG GGG ATC ATG AGG ATA TTT GCT GGC ATT ATA TTC ACA-3'; reverse 5'-TCA AGC TTG CAT GCC TTA CTT GTA CAG CTC GTC CA-3'. The primers were used to clone mB7-H1 into the lentiviral vector pSEW (Demaison et al., 2002) in front of the EGFP encoding sequence, already present in the pSEW vector. Coding sequences of B7-H1 are shown in italics. Following linearization of pSEW with BamHI, the amplified mB7-H1 fragment was inserted with the InFusion system (Takara Bio Europe, Saint-Germain-en-Laye, France). Correct sequence was verified by sequencing. For in vivo transduction of B7-H1 into the liver of mice, B7-H1 EGFP in the pSEW vector was subcloned into the pShuttle-CMV vector of the adEasy adenoviral vector system (Luo et al., 2007). The following primer pair was used containing flanking sequence appropriate InFusion cloning into the BglII/EcoRV site of pShuttle-CMV: forward 5'-GAT CCG CTA GAG ATC GCC ACC ATG AGG ATA TTT GCT GGC ATT ATA TTC ACA GC-3', reverse 5'-TCC GGT GGA TCG GAT TTA CTT GTA CAG CTC GTC CAT GCC-3'. Coding sequences of B7-H1 (forward primer) and EGFP (reverse primer) are displayed in italics. Correct sequence was verified by sequencing. As a negative control the pAdTrack vector, only encoding EGFP, was used.

For adenovirus preparation, Ad-293 cells were seeded in a 75 cm$^2$ flask in DMEM (high glucose, Glutamax)+10% FCS+pen/strep 1:100+HEPES 1:100+non-essential amino acids 1:100. After 4 days, cells were detached with 1 ml trypsin. 9 ml culture medium were added and cells were centrifuged at 500 g for 5 min. Following pellet resuspension in 10 ml of culture medium, 3.5 ml were seeded in 2×175 cm$^2$ flasks. After three days, cells were detached from both 175 cm$^2$ flasks with 1×2 ml trypsin. 9 ml medium were added, cells were spun and the pellet was resuspended and dispensed into 16×175 cm$^2$ flasks. 4 days later medium was removed from 100% confluent cells. In 8×50 ml tubes 29 ml and in 15 ml tube 7.5 ml warm culture medium was added. 0.5 ml of virus stock [1×10$^{11}$ particles/ml] was thawed at RT. The virus stock was added to the 15 ml tube and mixed by pipetting up/down. 1 ml of diluted adenovirus was transferred to each 50 ml tube. After tightly closing and mixing, 15 ml of diluted adenovirus was added to each flask. Flasks were incubated for 4 h in an incubator. Then, 15 ml prewarmed culture medium was added to each flask. After 3 days, most infected cells were detached as clusters. Non-infected cells were still spread-out and attached to the plastic. The medium was yellowish. Cells were detached by tapping the flasks against the hand. Medium was transferred into 10×50 ml tubes and spun at 500 g for 5 min at 4° C. Supernatant was discarded. Tubes were lightly shaken. 3×1 ml culture medium was transferred to 3 tubes. Using a 1 ml filter tip, first three pellets were resuspended in 1 ml culture medium. Resuspendend cells were transferred into a cryovial, which was snap-frozen in liquid N2 and transferred to a −80° C. freezer. To purify the adenoviral particle, cell lysates were prepared by putting cells of 10 vials through 4 rapid thaw/freeze cycles. Lysates were transferred into a 15 ml tube and spun at 1500 g for 10 min at 4° C. In the meantime, 6 CsCl gradients were prepared: To each ultracentrifuge tube 4 ml of 40% CsCl in PBS was added. Then, this was overlayed carefully with 4.5 ml 15% CsCl in PBS. The cleared cell lysate was transferred to a 50 ml tube, filled up to 18 ml with culture medium and mixed by pipetting. Three ml cleared lysate were transferred onto each CsCl gradient. Ultracentrifuge tubes were transferred into buckets of the rotor. The weight of corresponding bucket pairs was adjusted. CsCl gradients were centrifuged at 25,400 rpm for about 17 h at 4° C. Acceleration and deceleration were both set as 1. After centrifugation, tubes were carefully removed. Virus was collected by inserting a 23G needle connected to a 2 ml syringe below the lower virus band. Viruses from 3 ultracentrifuge tubes were collected and loaded into a 3 ml slide-a-lyzer cassette (10 kDa) (Thermo Scientifc, Darmstadt, Germany). The viral particles were dialyzed against 2 l cold PBS for 4 h. Then PBS was changed and dialyzing prolonged for 12 h. Afterwards, virus was collected and transferred to a 15 ml tube on ice. Aliquots were transferred to cryovials, snap-frozen and stored at −80° C. To determine the colony forming unit capacity, a plaque assay was applied. Evaluation was performed by fluorescence-microscopy due to the EGFP-tag of transduced genes. For mouse transduction, 5×1010 infectious particle were administered in 100 μl PBS.

For the cytotoxicity assay, CD8+ T cells derived from the spleen of C57Bl/6N OT-I mice (haplotype H-2b) as effector cells were co-incubated with Hepa1-6 cells, originating from the C57L strain (haplotype H-2b) as target cells for 24 h. Prior to this, Hepa1-6 cells were pulsed for 2 h with the ovalbumin (OVA) peptide 257-264 (AnaSpec, Fremont, U.S.A.), or the hepatitis B virus (HBV) peptide ILSPFLPLL derived from the HBsAg as control (IBA, Goettingen, Germany) or remained untreated as control. Following loading with antigen, Hepa1-6 cells were stained with Cell-Tracker™ Orange (Life Technologies GmbH, Frankfurt, Germany) before CD8+ T cell addition. After 24 h, surviving target cells were determined by FACS analyzes (FACS Fortessa, BD, Heidelberg, Germany).

Total RNA from 5*10$^5$ CD8+ T cells, Hepa1-6 cells, or primary liver cells was isolated by using peqGOLD RNAPure Kit (Peqlab, Erlangen, Germany) as instructed by the manufacturer's protocol. Two μg RNA was reverse transcribed into complementary DNA (cDNA) with the iScript™ cDNA Synthesis kit (Bio-Rad, Munich, Germany). Quantitative PCR (qPCR) was performed with the iQ™ SYBR® Green Supermix (Bio-Rad) according to the distributor's instructions. qPCR measurement and data analysis were performed with the CFX real-time PCR system from Bio-Rad. The following primer pairs (Biomers, Ulm, Germany) against murine targets were selected: B7-H1 (NM_21893) forward: 5'-TGC AGC AGT AAA CGC CTG CG-3', reverse: 5'CGC TGC CAA AGG ACC AGC TT-3'; IL-2 (NM_008366) forward: 5'TGA GCA TCC TGG GGA GTT TC-3', reverse: 5'-GTG ACC TCA AGT CCT GCA GG-3'; Fas-L (NM_010177) forward: 5'-ACC AAC CAA AGC CTT AAA-3', reverse: 5'-ATA CTT CAC TCC AGA GAT-3'; granzyme B (NM_013542) forward: 5'-CTC CAC GTG CTT TCA CCA AA-3', reverse: 5'-GGA AAA TAG TAC AGA GAG GCA-3'; perforin (NM_011073) forward: 5'-TGC TAC ACT GCC ACT CGG TCA-3', reverse: 5'-TTG GCT ACC TTG GAG TGG GAG-3'. IFNγ (NM_008337) forward: 5'-TTT GCA GCT CTT CCT CAT GG-3', reverse: 5'-TCG CCT TGC TGT TGC TGA AG-3'. Values were normalized to 18s rRNA.

All antibodies and secondary reagents were titrated to optimal concentrations. OT 1 CD8+ T cells were identified by FACS analysis utilizing anti-mouse V alpha 2 TCR FITC (eBioscience, San Diego, Calif., USA) as well as anti-mouse Vβ 5.1, 5.2 TCR-PE (BD Bioscience Heidelberg, Germany) antibodies. Fc receptor binding on OT 1 CD8+ T cells was blocked by CD16/CD32 anti mouse antibody for 15 min on ice followed by 20 min incubations of anti-CD8α-APC for T cells on ice. Surface expression of B7-H1 and B7-DC on the surface of primary hepatocytes was determined by FACS analysis, using anti-B7-H-PE or anti-B7-DC-PE. Immune cells were excluded by CD45-FITC staining, consequently analyzing CD45-cells only.

B7-H1, B7-DC, PD-1, Fas and EGFP expression were analyzed by Western analysis. Briefly, equivalent numbers of primary hepatocytes or Hepa1-6 cells were washed twice with PBS, lysed in RIPA buffer containing 1× complete Protease Inhibitor Cocktail Tablets (Roche, Basel, Switzerland) and sonicated for 10 impulses, followed by centrifugation for 10 min at 16.000 g (4° C.). Supernatants were denaturated with SDS-PAGE sample buffer (250 mM Tris pH 6.8, 40% glycerol, 10% 2-ME, 8% SDS, 0.02% bromphenol blue) for 10 minutes at 95° C. Comparable protein concentrations were maintained by Lowry (Bio-Rad). Proteins were separated on 10% SDS-polyacrylamide gels and transferred onto a nitrocellulose membrane by semi-dry blotting. Membranes were blocked with 5% BSA/TTBS followed by incubation with anti-B7-H1- (R&D systems), anti-B7-DC- (Santa Cruz), anti-PD-1- (Santa Cruz), a-Fas-antibody (Santa Cruz) in 5% BSA/TBS at 4° C. overnight. Loading was normalized to β-actin (anti-actin, Sigma-Aldrich). For protein detection, membrane was incubated with IRDye secondary antibodies (LI-COR, Bad Homburg, Germany) in 5% BSA/TTBS. Proteins were visualized and densitometrically analyzed with the Odyssey infrared imaging system.

Each experiment was performed at least three times. Statistical analysis was performed using the paired t-test. We considered P-values ≤0.05 as significant. Otherwise representative data are shown.

FULL CITATIONS OF THE REFERENCES CITED THROUGHOUT THE SPECIFICATION

Akiyama, T. E., S. Sakai, G. Lambert, C. J. Nicol, K. Matsusue, S. Pimprale, Y. H. Lee, M. Ricote, C. K. Glass, H. B. Brewer, Jr., and F. J. Gonzalez. 2002. Conditional disruption of the peroxisome proliferator-activated receptor gamma gene in mice results in lowered expression of ABCA1, ABCG1, and apoE in macrophages and reduced cholesterol efflux. *Mol Cell Biol* 22:2607-2619.

Angus, D. C., and T. van der Poll. 2013. Severe sepsis and septic shock. *N Engl J Med* 369:840-851.

Balk, R. A. 2004. Optimum treatment of severe sepsis and septic shock: evidence in support of the recommendations. *Dis Mon* 50:168-213.

Bettaieb, A., J. X. Jiang, Y. Sasaki, T. I. Chao, Z. Kiss, X. Chen, J. Tian, M. Katsuyama, C. Yabe-Nishimura, Y. Xi, C. Szyndralewiez, K. Schroder, A. Shah, R. P. Brandes, F. G. Haj, and N. J. Torok. 2015. Hepatocyte Nicotinamide Adenine Dinucleotide Phosphate Reduced Oxidase 4 Regulates Stress Signaling, Fibrosis, and Insulin Sensitivity During Development of Steatohepatitis in Mice. *Gastroenterology* doi:10.1053/j.gastro.2015.1004.1009.

Boudreau, H. E., S. U. Emerson, A. Korzeniowska, M. A. Jendrysik, and T. L. Leto. 2009. Hepatitis C virus (HCV) proteins induce NADPH oxidase 4 expression in a transforming growth factor beta-dependent manner: a new contributor to HCV-induced oxidative stress. *J Virol* 83:12934-12946.

Brune, B., N. Dehne, N. Grossmann, M. Jung, D. Namgaladze, T. Schmid, A. von Knethen, and A. Weigert. 2013. Redox control of inflammation in macrophages. *Antioxid Redox Signal* 19:595-637.

Butte, M. J., M. E. Keir, T. B. Phamduy, A. H. Sharpe, and G. J. Freeman. 2007. Programmed death-1 ligand 1 interacts specifically with the B7-1 costimulatory molecule to inhibit T cell responses. *Immunity* 27:111-122.

Chen, L. 2004. Co-inhibitory molecules of the B7-CD28 family in the control of T-cell immunity. *Nat Rev Immunol* 4:336-347.

Clark, M. A., L. D. Plank, A. B. Connolly, S. J. Streat, A. A. Hill, R. Gupta, D. N. Monk, A. Shenkin, and G. L. Hill. 1998. Effect of a chimeric antibody to tumor necrosis factor-alpha on cytokine and physiologic responses in patients with severe sepsis—a randomized, clinical trial. *Crit Care Med* 26:1650-1659.

Clarke, S. R., M. Barnden, C. Kurts, F. R. Carbone, J. F. Miller, and W. R. Heath. 2000. Characterization of the ovalbumin-specific TCR transgenic line OT-I: MHC elements for positive and negative selection. *Immunol Cell Biol* 78:110-117.

Cui, Y., K. Miyoshi, E. Claudio, U. K. Siebenlist, F. J. Gonzalez, J. Flaws, K. U. Wagner, and L. Hennighausen. 2002. Loss of the peroxisome proliferation-activated receptor gamma (PPARgamma) does not affect mammary development and propensity for tumor formation but leads to reduced fertility. *J Biol Chem* 277:17830-17835.

Darlington, G. J. 1987. Liver cell lines. *Methods Enzymol* 151:19-38.

del Rio, M. L., L. Buhler, C. Gibbons, J. Tian, and J. I. Rodriguez-Barbosa. 2008. PD-1/PD-L1, PD-1/PD-L2, and other co-inhibitory signaling pathways in transplantation. *Transpl Int* 21:1015-1028.

Dellinger, R. P., M. M. Levy, J. M. Carlet, J. Bion, M. M. Parker, R. Jaeschke, K. Reinhart, D. C. Angus, C. Brun-Buisson, R. Beale, T. Calandra, J. F. Dhainaut, H. Gerlach, M. Harvey, J. J. Marini, J. Marshall, M. Ranieri, G. Ramsay, J. Sevransky, B. T. Thompson, S. Townsend, J. S. Vender, J. L. Zimmerman, J. L. Vincent, C. International Surviving Sepsis Campaign Guidelines, N. American Association of Critical-Care, P. American College of Chest, P. American College of Emergency, S. Canadian Critical Care, M. European Society of Clinical, D. Infectious, M. European Society of Intensive Care, S. European Respiratory, F. International Sepsis, M. Japanese Association for Acute, M. Japanese Society of Intensive Care, M. Society of Critical Care, M. Society of Hospital, S. Surgical Infection, I. World Federation of Societies of, and M. Critical Care. 2008. Surviving Sepsis Campaign: international guidelines for management of severe sepsis and septic shock: 2008. *Crit Care Med* 36:296-327.

Demaison, C., K. Parsley, G. Brouns, M. Scherr, K. Battmer, C. Kinnon, M. Grez, and A. J. Thrasher. 2002. High-level transduction and gene expression in hematopoietic repopulating cells using a human immunodeficiency [correction of imunodeficiency] virus type 1-based lentiviral vector containing an internal spleen focus forming virus promoter. *Hum Gene Ther* 13:803-813.

Diaz-Cruz, A., M. M. Vilchis-Landeros, R. Guinzberg, R. Villalobos-Molina, and E. Pina. 2011. NOX2 activated by alpha1-adrenoceptors modulates hepatic metabolic routes stimulated by beta-adrenoceptors. *Free Radic Res* 45:1366-1378.

Dikalov, S. I., A. E. Dikalova, A. T. Bikineyeva, H. H. Schmidt, D. G. Harrison, and K. K. Griendling. 2008. Distinct roles of Nox1 and Nox4 in basal and angiotensin II-stimulated superoxide and hydrogen peroxide production. *Free Radic Biol Med* 45:1340-1351.

Docke, W. D., F. Randow, U. Syrbe, D. Krausch, K. Asadullah, P. Reinke, H. D. Volk, and W. Kox. 1997. Monocyte deactivation in septic patients: restoration by IFN-gamma treatment. *Nat Med* 3:678-681.

Drummond, G. R., and C. G. Sobey. 2014. Endothelial NADPH oxidases: which NOX to target in vascular disease? *Trends Endocrinol Metab* 25:452-463.

Fife, B. T., K. E. Pauken, T. N. Eagar, T. Obu, J. Wu, Q. Tang, M. Azuma, M. F. Krummel, and J. A. Bluestone. 2009. Interactions between PD-1 and PD-L1 promote tolerance by blocking the TCR-induced stop signal. *Nat Immunol* 10:1185-1192.

Galle, P. R., W. J. Hofmann, H. Walczak, H. Schaller, G. Otto, W. Stremmel, P. H. Krammer, and L. Runkel. 1995. Involvement of the CD95 (APO-1/Fas) receptor and ligand in liver damage. *J Exp Med* 182:1223-1230.

Hanabuchi, S., M. Koyanagi, A. Kawasaki, N. Shinohara, A. Matsuzawa, Y. Nishimura, Y. Kobayashi, S. Yonehara, H. Yagita, and K. Okumura. 1994. Fas and its ligand in a general mechanism of T-cell-mediated cytotoxicity. *Proc Natl Acad Sci USA* 91:4930-4934.

Hennet, T., F. K. Hagen, L. A. Tabak, and J. D. Marth. 1995. T-cell-specific deletion of a polypeptide N-acetylgalactosaminyl-transferase gene by site-directed recombination. *Proc Natl Acad Sci USA* 92:12070-12074.

Hotchkiss, R. S., and I. E. Karl. 2003. The pathophysiology and treatment of sepsis. *N Engl J Med* 348:138-150.

Hotchkiss, R. S., K. W. McConnell, K. Bullok, C. G. Davis, K. C. Chang, S. J. Schwulst, J. C. Dunne, G. P. Dietz, M. Bahr, J. E. McDunn, I. E. Karl, T. H. Wagner, J. P. Cobb, C. M. Coopersmith, and D. Piwnica-Worms. 2006. TAT-BH4 and TAT-Bcl-xL peptides protect against sepsis-induced lymphocyte apoptosis in vivo. *J Immunol* 176:5471-5477.

Hotchkiss, R. S., and S. Opal. 2010. Immunotherapy for sepsis—a new approach against an ancient foe. *N Engl J Med* 363:87-89.

Hume, D. A. 2011. Applications of myeloid-specific promoters in transgenic mice support in vivo imaging and functional genomics but do not support the concept of distinct macrophage and dendritic cell lineages or roles in immunity. *J Leukoc Biol* 89:525-538.

Jiang, J. X., X. Chen, N. Serizawa, C. Szyndralewiez, P. Page, K. Schroder, R. P. Brandes, S. Devaraj, and N. J. Torok. 2012. Liver fibrosis and hepatocyte apoptosis are attenuated by GKT137831, a novel NOX4/NOX1 inhibitor in vivo. *Free Radic Biol Med* 53:289-296.

Kaukonen, K. M., M. Bailey, S. Suzuki, D. Pilcher, and R. Bellomo. 2014. Mortality related to severe sepsis and septic shock among critically ill patients in Australia and New Zealand, 2000-2012. *JAMA* 311:1308-1316.

Luo, J., Z. L. Deng, X. Luo, N. Tang, W. X. Song, J. Chen, K. A. Sharff, H. H. Luu, R. C. Haydon, K. W. Kinzler, B. Vogelstein, and T. C. He. 2007. A protocol for rapid generation of recombinant adenoviruses using the AdEasy system. *Nat Protoc* 2:1236-1247.

Marquez-Velasco, R., R. Bojalil, A. Buelna, F. Flores-Guzman, J. Estevez-Ramirez, J. Laguna, A. M. Hernandez, A. Diaz-Quinonez, and J. F. Paniagua-Solis. 2006. Anti-tumor necrosis factor alpha F(ab')2 antibody fragments protect in murine polymicrobial sepsis: concentration and early intervention are fundamental to the outcome. *Inflamm Res* 55:378-384.

Matsumura, T., A. Ito, T. Takii, H. Hayashi, and K. Onozaki. 2000. Endotoxin and cytokine regulation of toll-like receptor (TLR) 2 and TLR4 gene expression in murine liver and hepatocytes. *J Interferon Cytokine Res* 20:915-921.

Meisel, C., J. C. Schefold, R. Pschowski, T. Baumann, K. Hetzger, J. Gregor, S. Weber-Carstens, D. Hasper, D. Keh, H. Zuckermann, P. Reinke, and H. D. Volk. 2009. Granulocyte-macrophage colony-stimulating factor to reverse sepsis-associated immunosuppression: a double-blind, randomized, placebo-controlled multicenter trial. *Am J Respir Crit Care Med* 180:640-648.

Munford, R. S., and J. Pugin. 2001. Normal responses to injury prevent systemic inflammation and can be immunosuppressive. *Am J Respir Crit Care Med* 163:316-321.

Ostrand-Rosenberg, S., L. A. Horn, and S. T. Haile. 2014. The programmed death-1 immune-suppressive pathway: barrier to antitumor immunity. *J Immuno* 1193:3835-3841.

Otto, G. P., M. Sossdorf, R. A. Claus, J. Rodel, K. Menge, K. Reinhart, M. Bauer, and N. C. Riedemann. 2011. The late phase of sepsis is characterized by an increased microbiological burden and death rate. *Crit Care* 15:R183.

Pangault, C., Y. Le Tulzo, P. Tattevin, V. Guilloux, N. Bescher, and B. Drenou. 2006. Down-modulation of granulocyte macrophage-colony stimulating factor receptor on monocytes during human septic shock. *Crit Care Med* 34:1193-1201.

Paterson, R. L., H. F. Galley, and N. R. Webster. 2003. The effect of N-acetylcysteine on nuclear factor-kappa B activation, interleukin-6, interleukin-8, and intercellular adhesion molecule-1 expression in patients with sepsis. *Crit Care Med* 31:2574-2578.

Reinhart, K., T. Menges, B. Gardlund, J. Harm Zwaveling, M. Smithes, J. L. Vincent, J. M. Tellado, A. Salgado-Remigio, R. Zimlichman, S. Withington, K. Tschaikowsky, R. Brase, P. Damas, H. Kupper, J. Kempeni, J. Eiselstein, and M. Kaul. 2001. Randomized, placebo-controlled trial of the anti-tumor necrosis factor antibody fragment afelimomab in hyperinflammatory response during severe sepsis: The RAMSES Study. *Crit Care Med* 29:765-769.

Rittirsch, D., M. S. Huber-Lang, M. A. Flierl, and P. A. Ward. 2009. Immunodesign of experimental sepsis by cecal ligation and puncture. *Nat Protoc* 4:31-36.

Romics, L., Jr., A. Dolganiuc, K. Kodys, Y. Drechsler, S. Oak, A. Velayudham, P. Mandrekar, and G. Szabo. 2004. Selective priming to Toll-like receptor 4 (TLR4), not TLR2, ligands by *P. acnes* involves up-regulation of MD-2 in mice. *Hepatology* 40:555-564.

Schmidt, M. V., P. Paulus, A. M. Kuhn, A. Weigert, V. Morbitzer, K. Zacharowski, V. A. Kempf, B. Brune, and A. von Knethen. 2011. Peroxisome proliferator-activated receptor gamma-induced T cell apoptosis reduces survival during polymicrobial sepsis. *Am J Respir Crit Care Med* 184:64-74.

Seki, E., and D. A. Brenner. 2008. Toll-like receptors and adaptor molecules in liver disease: update. *Hepatology* 48:322-335.

Sharpe, A. H., E. J. Wherry, R. Ahmed, and G. J. Freeman. 2007. The function of programmed cell death 1 and its ligands in regulating autoimmunity and infection. *Nat Immunol* 8:239-245.

Spencer, N. Y., W. Zhou, Q. Li, Y. Zhang, M. Luo, Z. Yan, T. J. Lynch, D. Abbott, B. Banfi, and J. F. Engelhardt. 2013. Hepatocytes produce TNF-alpha following hypoxia-reoxygenation and liver ischemia-reperfusion in a NADPH oxidase- and c-Src-dependent manner. *Am J Physiol Gastrointest Liver Physiol* 305:G84-94.

Sunshine, J., and J. M. Taube. 2015. PD-1/PD-L1 inhibitors. *Curr Opin Pharmacol* 23:32-38.

Szakmany, T., B. Hauser, and P. Radermacher. 2012. N-acetylcysteine for sepsis and systemic inflammatory response in adults. *Cochrane Database Syst Rev* 9:CD006616.

Thomson, A. W., and P. A. Knolle. 2010. Antigen-presenting cell function in the tolerogenic liver environment. *Nat Rev Immunol* 10:753-766.

Topalian, S. L., C. G. Drake, and D. M. Pardoll. 2012. Targeting the PD-1/B7-H1(PD-L1) pathway to activate anti-tumor immunity. *Curr Opin Immunol* 24:207-212.

Torgersen, C., P. Moser, G. Luckner, V. Mayr, S. Jochberger, W. R. Hasibeder, and M. W. Dunser. 2009. Macroscopic postmortem findings in 235 surgical intensive care patients with sepsis. *Anesth Analg* 108:1841-1847.

Ueki, S., A. Castellaneta, O. Yoshida, K. Ozaki, M. Zhang, S. Kimura, K. Isse, M. Ross, L. Shao, D. B. Stolz, A. W. Thomson, A. J. Demetris, D. A. Geller, and N. Murase. 2011. Hepatic B7 homolog 1 expression is essential for controlling cold ischemia/reperfusion injury after mouse liver transplantation. *Hepatology* 54:216-228.

van Dijk, K. W., K. E. Kypreos, F. J. Fallaux, and J. Hageman. 2011. Adenovirus-mediated gene transfer. *Methods Mol Biol* 693:321-343.

Venner, J. M., K. S. Famulski, D. Badr, L. G. Hidalgo, J. Chang, and P. F. Halloran. 2014. Molecular landscape of T cell-mediated rejection in human kidney transplants: prominence of CTLA4 and PD ligands. *Am J Transplant* 14:2565-2576.

Vincent, J. L., J. C. Marshall, S. A. Namendys-Silva, B. Francois, I. Martin-Loeches, J. Lipman, K. Reinhart, M. Antonelli, P. Pickkers, H. Njimi, E. Jimenez, Y. Sakr, and I. investigators. 2014. Assessment of the worldwide burden of critical illness: the intensive care over nations (ICON) audit. *Lancet Respir Med* 2:380-386.

Vincent, J. L., S. M. Opal, J. C. Marshall, and K. J. Tracey. 2013. Sepsis definitions: time for change. *Lancet* 381: 774-775.

von Knethen, A., L. K. Sha, T. Knape, L. Kuchler, A. K. Giegerich, M. Schulz, I. A. Hauser, and B. Brune. 2015. Activation of the peroxisome proliferator-activated receptor gamma counteracts sepsis-induced T cell cytotoxicity toward alloantigenic target cells. *J Mol Med* (Berl) 93:633-644.

Wesche-Soldato, D. E., C. S. Chung, S. H. Gregory, T. P. Salazar-Mather, C. A. Ayala, and A. Ayala. 2007a. CD8+ T cells promote inflammation and apoptosis in the liver after sepsis: role of Fas-FasL. *Am J Pathol* 171:87-96.

Wesche-Soldato, D. E., R. Z. Swan, C. S. Chung, and A. Ayala. 2007b. The apoptotic pathway as a therapeutic target in sepsis. *Curr Drug Targets* 8:493-500.

---

The invention claimed is:

1. A method of at least one of treating or preventing cytotoxic T-cell dependent liver damage in a subject suffering from sepsis, said method comprising (a) administering to said subject a therapeutically effective amount of a fusion polypeptide comprising at least (i) a first portion being an Fc portion of an immunoglobulin and (ii) a second portion comprising the extracellular portion of the human B7-H1 polypeptide or a variant thereof or (b) administering a therapeutically effective amount of a polynucleotide encoding said fusion polypeptide, wherein said administering in (a) or (b) is administering within twenty-four hours of diagnosis of sepsis in said subject.

2. The method according to claim 1, wherein said liver damage is CD8 cytotoxic T-cell dependent liver damage.

3. The method according to claim 1, wherein said immunoglobulin is human IgG.

4. The method according to claim 1, wherein said extracellular portion of the human B7-H1 polypeptide or variant thereof is selected from the group consisting of:
   (a) a polypeptide having an amino acid sequence encoded by the nucleic acid sequence shown in SEQ ID NO: 1;
   (b) a polypeptide having an amino acid sequence shown in SEQ ID NO: 2;
   (c) a polypeptide remaining capable of binding to the PD1 polypeptide and having an amino acid sequence which is at least 70% identical to the amino acid sequence of the polypeptide of (a) or (b), and
   (d) a polypeptide remaining capable of binding to the PD1 polypeptide having an amino acid sequence that is a variant of the polypeptide of (a) or (b) comprising at least one of the following amino acid exchanges from the polypeptide of (a) or (b): L27A, S34Y, D49S, Y56S, E58S, K62S, H69F, E72S, K75S, K89S, A98F, Q100S, R113Y, and S117Y.

5. The method according to claim 1, wherein said at least the first portion and at least the second portion are permanently or reversibly linked to each other.

6. The method according to claim 1, wherein said subject is a mammal, preferably a human.

7. The method according to claim 1, wherein said fusion polypeptide is to be applied once as a bolus or is to be applied at least twice.

8. The method according to claim 1, wherein said fusion polypeptide is to be applied together with at least one further drug.

9. The method according to claim 8, wherein said at least one further drug is selected from the group consisting of: antibiotics, vasopressors, steroids, anticoagulants, antithrombotics, proinflammatory cytokines and DAMP inhibitors.

10. The method according to claim 1, wherein said fusion polypeptide upon administration inhibits sepsis-induced cytotoxic T-cells in the subject.

11. The method according to claim 1, wherein said fusion polypeptide upon administration induces a long-lasting tolerance in cytotoxic T-cells in the subject against sepsis-caused activation.

12. The method according to claim 1, wherein said extracellular portion of the human B7-H1 polypeptide or variant thereof is selected from the group consisting of:
   (a) a polypeptide having an amino acid sequence encoded by the nucleic acid sequence shown in SEQ ID NO: 5;
   (b) a polypeptide having an amino acid sequence shown in SEQ ID NO: 6;
   (c) a polypeptide remaining capable of binding to the PD1 polypeptide and having an amino acid sequence which is at least 70% identical to the amino acid sequence of the polypeptide of (a) or (b), and
   (d) a polypeptide remaining capable of binding to the PD1 polypeptide having an amino acid sequence that is a variant of the polypeptide of (a) or (b) comprising at least one of the following amino acid exchanges from the polypeptide of (a) or (b): L27A, S34Y, D49S, Y56S, E58S, K62S, A69F, E72S, K75S, K89S, A98F, Q100S, C113Y, and S117Y.

* * * * *